US011510827B2

(12) United States Patent
Seitz et al.

(10) Patent No.: US 11,510,827 B2
(45) Date of Patent: *Nov. 29, 2022

(54) LENGTH-TO-SIDE SILHOUETTES OF ADULT DISPOSABLE ABSORBENT ARTICLES AND ARRAYS

(71) Applicant: The Procter & Gamble Company, Cincinnati, OH (US)

(72) Inventors: Bret Darren Seitz, West Chester, OH (US); Gary Dean LaVon, Liberty Township, OH (US); Jill Trygier, West Chester, OH (US); Vanessa Melendez, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 417 days.

This patent is subject to a terminal disclaimer.

(21) Appl. No.: 16/594,205

(22) Filed: Oct. 7, 2019

(65) Prior Publication Data

US 2020/0030156 A1 Jan. 30, 2020

Related U.S. Application Data

(63) Continuation of application No. 14/699,145, filed on Apr. 29, 2015, now Pat. No. 10,478,352.

(Continued)

(51) Int. Cl.
*A61F 13/49* (2006.01)
*A61F 13/496* (2006.01)
(Continued)

(52) U.S. Cl.
CPC ............ *A61F 13/49* (2013.01); *A61F 13/491* (2013.01); *A61F 13/496* (2013.01);
(Continued)

(58) Field of Classification Search
CPC .. A61F 13/49; A61F 13/49011; A61F 13/491; A61F 13/496; A61F 13/4963;
(Continued)

(56) References Cited

U.S. PATENT DOCUMENTS 414,637 A 11/1889 Goodson
416,794 A 12/1889 Mathieu
(Continued)

FOREIGN PATENT DOCUMENTS

EP 1 174 104 1/2002
EP 1447067 A1 8/2004
(Continued)

OTHER PUBLICATIONS

"Brand Architecture Basics: What Is a Sub-Brand?" https://distility.com/building-brand/brand-architecture-basics-what-is-an-overbrand/, Sep. 27, 2011.
(Continued)

*Primary Examiner* — Michele M Kidwell
(74) *Attorney, Agent, or Firm* — Charles R. Matson; Richard L. Alexander

(57) ABSTRACT

An array of packages may comprise two or more different sizes of disposable absorbent articles. The second absorbent article may have a larger Relaxed Product Side Length than the first absorbent article and/or a larger Relaxed Product Length than the first absorbent article.

18 Claims, 22 Drawing Sheets

Related U.S. Application Data

(60) Provisional application No. 61/990,365, filed on May 8, 2014.

(51) Int. Cl.
*A61F 13/491* (2006.01)
*A61F 13/551* (2006.01)

(52) U.S. Cl.
CPC .... *A61F 13/49011* (2013.01); *A61F 13/4963* (2013.01); *A61F 13/55105* (2013.01); *A61F 2013/49092* (2013.01); *A61F 2013/49098* (2013.01)

(58) Field of Classification Search
CPC ...... A61F 13/55105; A61F 2013/49092; A61F 2013/49098
See application file for complete search history.

(56) References Cited

U.S. PATENT DOCUMENTS

| | | | |
|---|---|---|---|
| 421,901 A | 2/1890 | Breher | |
| 421,902 A | 2/1890 | Britz | |
| 437,686 A | 10/1890 | Geddes | |
| 443,451 A | 12/1890 | Hunter | |
| 443,508 A | 12/1890 | Emmet | |
| 445,329 A | 1/1891 | Kerr | |
| 451,279 A | 4/1891 | Sailor | |
| 3,815,602 A | 6/1974 | Johns et al. | |
| 3,967,756 A | 7/1976 | Barish | |
| 3,982,659 A | 9/1976 | Ross | |
| 3,994,417 A | 11/1976 | Boedecker | |
| 4,117,187 A | 9/1978 | Adams et al. | |
| 4,230,113 A | 10/1980 | Mehta | |
| 4,299,223 A | 11/1981 | Cronkrite | |
| 4,471,881 A | 9/1984 | Foster | |
| 4,706,845 A | 11/1987 | Schnurer et al. | |
| 4,840,270 A | 6/1989 | Caputo et al. | |
| 4,940,464 A | 7/1990 | Van Gompel | |
| 4,966,286 A | 10/1990 | Muckenfuhs | |
| 4,971,220 A | 11/1990 | Kaufman et al. | |
| 5,050,737 A | 9/1991 | Joslyn et al. | |
| 5,065,868 A | 11/1991 | Cornelissen et al. | |
| 5,151,092 A | 9/1992 | Buell et al. | |
| 5,231,266 A | 7/1993 | Warren | |
| 5,242,057 A | 9/1993 | Cook et al. | |
| 5,261,901 A | 11/1993 | Guay | |
| 5,284,263 A | 2/1994 | Papciak | |
| 5,322,178 A | 6/1994 | Foos | |
| 5,366,104 A | 11/1994 | Armstrong | |
| 5,368,188 A | 11/1994 | Twardowski | |
| 5,377,853 A | 1/1995 | Papciak | |
| 5,395,358 A | 3/1995 | Lu | |
| 5,413,849 A | 5/1995 | Austin et al. | |
| 5,443,161 A | 8/1995 | Jonese | |
| 5,485,919 A | 1/1996 | Samberg et al. | |
| 5,507,736 A | 4/1996 | Clear | |
| 5,569,234 A | 10/1996 | Buell et al. | |
| 5,575,783 A | 11/1996 | Clear et al. | |
| 5,591,155 A | 1/1997 | Nishikawa et al. | |
| 5,599,620 A | 2/1997 | Huskey | |
| 5,647,506 A | 7/1997 | Julius | |
| 5,678,727 A | 10/1997 | Rice | |
| 5,690,627 A | 11/1997 | Clear et al. | |
| 5,715,841 A | 2/1998 | Utecht | |
| 5,732,716 A | 3/1998 | Utecht | |
| 5,735,839 A | 4/1998 | Kawaguchi et al. | |
| 5,746,730 A | 5/1998 | Suzuki et al. | |
| 5,785,179 A | 7/1998 | Buczwinski et al. | |
| 5,791,465 A | 8/1998 | Niki et al. | |
| 5,839,585 A | 11/1998 | Miller | |
| 5,865,322 A | 2/1999 | Miller | |
| 5,885,264 A | 3/1999 | Matsushita | |
| 5,938,648 A | 8/1999 | LaVon et al. | |
| 5,944,237 A | 8/1999 | Gouldson | |
| 5,947,302 A | 9/1999 | Miller | |
| 6,013,590 A | 1/2000 | Noda | |
| 6,024,094 A | 2/2000 | Utecht | |
| 6,050,985 A | 4/2000 | LaVon et al. | |
| 6,075,178 A | 6/2000 | Wilhelm et al. | |
| 6,092,690 A | 7/2000 | Bitowft et al. | |
| 6,168,022 B1 | 1/2001 | Ward et al. | |
| 6,190,369 B1 | 2/2001 | Palumbo et al. | |
| 6,195,800 B1 | 3/2001 | Gilmer et al. | |
| 6,229,061 B1 | 5/2001 | Dragoo et al. | |
| 6,258,077 B1 | 7/2001 | Buell et al. | |
| 6,269,969 B1 | 8/2001 | Huang et al. | |
| 6,269,970 B1 | 8/2001 | Huang et al. | |
| 6,274,218 B1 | 8/2001 | Shingo | |
| 6,296,144 B1 | 10/2001 | Tanaka et al. | |
| 6,302,871 B1 | 10/2001 | Nakao et al. | |
| 6,315,114 B1 | 11/2001 | Keck et al. | |
| 6,361,784 B1 | 3/2002 | Brennan et al. | |
| 6,401,968 B1 | 6/2002 | Huang et al. | |
| 6,412,634 B1 | 7/2002 | Telesca et al. | |
| 6,454,095 B1 | 9/2002 | Brisebois et al. | |
| 6,488,202 B1 | 12/2002 | Seitz et al. | |
| 6,491,165 B2 | 12/2002 | Kuske et al. | |
| 6,500,444 B1 | 12/2002 | Ferenc et al. | |
| 6,520,946 B1 | 2/2003 | Krueger | |
| 6,568,530 B2 | 5/2003 | Takahashi et al. | |
| 6,581,775 B1 | 6/2003 | Hagopian | |
| 6,601,705 B2 | 8/2003 | Molina et al. | |
| 6,612,846 B1 | 9/2003 | Underhill et al. | |
| 6,648,864 B2 | 11/2003 | Ronn et al. | |
| 6,649,808 B1 | 11/2003 | Tao | |
| 6,667,464 B2 | 12/2003 | Ellis | |
| 6,763,944 B2 | 7/2004 | Ronn et al. | |
| 6,830,755 B2 | 12/2004 | Librizzi et al. | |
| 6,837,395 B2 | 1/2005 | Windorski et al. | |
| 6,911,022 B2 | 6/2005 | Steger et al. | |
| 7,008,685 B2 | 3/2006 | Groitzsch et al. | |
| 7,118,558 B2 | 10/2006 | Wu | |
| 7,222,732 B2 | 5/2007 | Ronn et al. | |
| 7,549,538 B2 | 6/2009 | Naoe et al. | |
| 7,572,249 B2 | 8/2009 | Betts | |
| 7,582,075 B2 | 9/2009 | Betts et al. | |
| 7,770,729 B2 | 8/2010 | Warren et al. | |
| 7,824,389 B2 | 11/2010 | Veith | |
| 7,863,497 B2 | 1/2011 | Magee et al. | |
| 7,931,632 B2 | 4/2011 | Betts | |
| 7,959,621 B2 | 6/2011 | Ashton et al. | |
| 7,998,127 B2 | 8/2011 | Betts | |
| 8,069,982 B2 | 12/2011 | Ronn et al. | |
| 8,079,994 B2 | 12/2011 | Richlen | |
| 8,092,438 B2 | 1/2012 | Betts et al. | |
| 8,220,632 B2 | 7/2012 | Oi et al. | |
| 8,226,625 B2 | 7/2012 | Turner et al. | |
| 8,273,067 B2 | 9/2012 | Cohen | |
| 8,388,594 B2 | 3/2013 | Turner et al. | |
| 8,435,222 B2 | 5/2013 | Ronn et al. | |
| 8,480,642 B2 | 7/2013 | Betts | |
| 8,518,004 B2 | 8/2013 | Betts et al. | |
| 8,568,566 B2 | 10/2013 | Jackels et al. | |
| 8,834,436 B2 | 9/2014 | Ronn et al. | |
| 9,028,462 B2 | 5/2015 | Poole et al. | |
| 9,039,669 B1 | 5/2015 | LaVon et al. | |
| 9,216,118 B2 | 12/2015 | Roe et al. | |
| 9,254,228 B2 | 2/2016 | Ashton | |
| 9,474,657 B2 | 10/2016 | Berrizbeitia et al. | |
| 9,622,922 B2 | 4/2017 | Nelson | |
| 9,649,232 B2 | 5/2017 | Hippe et al. | |
| 2001/0021833 A1 | 9/2001 | Schmidt et al. | |
| 2001/0055609 A1 | 12/2001 | Shantz et al. | |
| 2002/0002358 A1 | 1/2002 | Durrance et al. | |
| 2002/0004527 A1 | 1/2002 | Auestad et al. | |
| 2002/0052588 A1 | 5/2002 | Otsubu | |
| 2002/0064323 A1 | 5/2002 | Chin | |
| 2002/0072723 A1 | 6/2002 | Ronn et al. | |
| 2002/0148742 A1 | 10/2002 | Bisbal et al. | |
| 2002/0151858 A1 | 10/2002 | Karami et al. | |
| 2002/0164910 A1 | 11/2002 | Murray | |
| 2002/0173767 A1 | 11/2002 | Popp et al. | |
| 2002/0177829 A1 | 11/2002 | Fell et al. | |

(56) References Cited

U.S. PATENT DOCUMENTS

| | | |
|---|---|---|
| 2002/0183712 A1 | 12/2002 | Datta et al. |
| 2003/0019508 A1 | 1/2003 | Tomarchio et al. |
| 2003/0073966 A1 | 4/2003 | Sosalla |
| 2003/0084984 A1 | 5/2003 | Glaug et al. |
| 2003/0097109 A1 | 5/2003 | Bruce |
| 2003/0114808 A1 | 6/2003 | Underhill et al. |
| 2003/0120231 A1 | 6/2003 | Wang et al. |
| 2003/0135184 A1 | 7/2003 | Van Gompel et al. |
| 2003/0135186 A1 | 7/2003 | Olson et al. |
| 2003/0136704 A1 | 7/2003 | Burgess |
| 2003/0139713 A1 | 7/2003 | Olson et al. |
| 2003/0158532 A1 | 8/2003 | Magee et al. |
| 2003/0181883 A1 | 9/2003 | Olson et al. |
| 2003/0226266 A1 | 12/2003 | Ellis |
| 2003/0229327 A1 | 12/2003 | Imsangjan et al. |
| 2004/0006323 A1 | 1/2004 | Hall et al. |
| 2004/0010240 A1 | 1/2004 | Ronn et al. |
| 2004/0030308 A1 | 2/2004 | Ronn et al. |
| 2004/0030317 A1 | 2/2004 | Torigoshi et al. |
| 2004/0052834 A1 | 3/2004 | West et al. |
| 2004/0064126 A1 | 4/2004 | Fletcher |
| 2004/0087928 A1 | 5/2004 | Ducker |
| 2004/0092904 A1 | 5/2004 | De, Jr. et al. |
| 2004/0097895 A1 | 5/2004 | Busam |
| 2004/0097897 A1 | 7/2004 | Ronn et al. |
| 2004/0127865 A1 | 7/2004 | Mitsui et al. |
| 2004/0133180 A1 | 7/2004 | Mori et al. |
| 2004/0162536 A1 | 8/2004 | Becker et al. |
| 2004/0219854 A1 | 11/2004 | Groitzsch et al. |
| 2004/0243083 A1 | 12/2004 | Matsuda et al. |
| 2004/0243093 A1 | 12/2004 | Berenson et al. |
| 2004/0249354 A1 | 12/2004 | Matsuda et al. |
| 2005/0059943 A1 | 3/2005 | Suzuki et al. |
| 2005/0065492 A1 | 3/2005 | Cole et al. |
| 2005/0074483 A1 | 4/2005 | Lange |
| 2005/0085782 A1 | 4/2005 | Popp et al. |
| 2005/0102735 A1 | 5/2005 | Popp et al. |
| 2005/0121347 A1 | 6/2005 | Hanson |
| 2005/0133387 A1 | 6/2005 | Cohen et al. |
| 2005/0142336 A1 | 6/2005 | Romano, III et al. |
| 2005/0148983 A1 | 7/2005 | Doverbo et al. |
| 2005/0210566 A1 | 9/2005 | Mortell et al. |
| 2005/0256493 A1 | 11/2005 | Datta et al. |
| 2005/0256758 A1 | 11/2005 | Sierra et al. |
| 2005/0267431 A1 | 12/2005 | Sasaki et al. |
| 2006/0052763 A1 | 3/2006 | Tachibana |
| 2006/0069372 A1 | 3/2006 | Chakravarty |
| 2006/0082133 A1 | 4/2006 | Naoe et al. |
| 2006/0173695 A1 | 8/2006 | Brandt |
| 2006/0183086 A1 | 8/2006 | Brandt |
| 2006/0186132 A1 | 8/2006 | Panning et al. |
| 2006/0193898 A1 | 8/2006 | Norman |
| 2006/0195357 A1 | 8/2006 | Klofta et al. |
| 2006/0229581 A1 | 10/2006 | Ulas et al. |
| 2006/0241558 A1 | 10/2006 | Ramshak |
| 2007/0016158 A1 | 1/2007 | Endres |
| 2007/0032768 A1 | 2/2007 | Cohen et al. |
| 2007/0043331 A1 | 2/2007 | Haruki et al. |
| 2007/0141311 A1 | 6/2007 | Mleziva et al. |
| 2007/0142798 A1 | 6/2007 | Goodlander et al. |
| 2007/0151182 A1 | 7/2007 | Ronn et al. |
| 2007/0235263 A1 | 10/2007 | Legault et al. |
| 2007/0255248 A1 | 11/2007 | Hendren et al. |
| 2007/0287975 A1 | 12/2007 | Fujimoto et al. |
| 2007/0287983 A1 | 12/2007 | Lodge et al. |
| 2007/0293833 A1 | 12/2007 | Wennerback |
| 2008/0051747 A1 | 2/2008 | Cohen |
| 2008/0082070 A1 | 4/2008 | Fell et al. |
| 2008/0110782 A1 | 5/2008 | Burgdorf et al. |
| 2008/0128308 A1 | 6/2008 | Betts |
| 2008/0195070 A1 | 8/2008 | Ponomarenk et al. |
| 2008/0208155 A1 | 8/2008 | LaVon et al. |
| 2008/0234643 A1 | 9/2008 | Kaneda |
| 2008/0312624 A1 | 12/2008 | Hundorf et al. |
| 2009/0030389 A1 | 1/2009 | Ashton et al. |
| 2009/0088718 A1 | 4/2009 | Toyoshima et al. |
| 2009/0240221 A1 | 9/2009 | Rothenberger et al. |
| 2009/0266733 A1 | 10/2009 | Betts et al. |
| 2009/0326504 A1 | 12/2009 | Kaneda |
| 2010/0022151 A1 | 1/2010 | Malowaniec |
| 2010/0057029 A1 | 3/2010 | Popp et al. |
| 2010/0106123 A1 | 4/2010 | Fukas |
| 2010/0108554 A1 | 5/2010 | Melius et al. |
| 2010/0130956 A1 | 5/2010 | Wennerback |
| 2010/0181223 A1 | 7/2010 | Warren et al. |
| 2010/0292666 A1 | 11/2010 | Olson et al. |
| 2011/0077609 A1 | 3/2011 | Kuwano et al. |
| 2011/0088828 A1 | 4/2011 | Misek et al. |
| 2011/0098668 A1 | 4/2011 | Thorson et al. |
| 2011/0144602 A1 | 6/2011 | Long |
| 2011/0160687 A1 | 6/2011 | Welch et al. |
| 2011/0288517 A1 | 11/2011 | Mori |
| 2012/0083758 A1 | 4/2012 | Ronn et al. |
| 2012/0157959 A1 | 6/2012 | Kline et al. |
| 2012/0215191 A1 | 8/2012 | Takino |
| 2012/0271267 A1 | 10/2012 | Love et al. |
| 2012/0296293 A1 | 11/2012 | Clifford |
| 2013/0018351 A1 | 1/2013 | Desai |
| 2013/0041340 A1 | 2/2013 | Kawakami et al. |
| 2013/0072887 A1 | 3/2013 | LaVon et al. |
| 2013/0138072 A1 | 5/2013 | Morimoto et al. |
| 2013/0165895 A1 | 6/2013 | Wennerback |
| 2013/0211355 A1 | 8/2013 | Nishikawa et al. |
| 2013/0211356 A1 | 8/2013 | Nishikawa et al. |
| 2013/0211357 A1 | 8/2013 | Nishikawa et al. |
| 2013/0211363 A1 | 8/2013 | LaVon et al. |
| 2013/0226127 A1 | 8/2013 | Takahashi et al. |
| 2013/0233749 A1 | 9/2013 | Ronn et al. |
| 2013/0281954 A1 | 10/2013 | Ishihara et al. |
| 2013/0306226 A1 | 11/2013 | Zink et al. |
| 2013/0310795 A1 | 11/2013 | Glahn et al. |
| 2014/0005628 A1 | 1/2014 | Lavon et al. |
| 2014/0013490 A1 | 1/2014 | Evenson et al. |
| 2014/0018759 A1 | 1/2014 | Jayasinghe et al. |
| 2014/0163506 A1 | 6/2014 | Roe et al. |
| 2014/0171892 A1 | 6/2014 | Ichikawa et al. |
| 2014/0224695 A1 | 8/2014 | Ronn et al. |
| 2014/0288519 A1 | 9/2014 | Schmitz et al. |
| 2014/0288523 A1 | 9/2014 | Hasse et al. |
| 2014/0350508 A1 | 11/2014 | Popp et al. |
| 2014/0371701 A1 | 12/2014 | Bianichi |
| 2014/0378932 A1 | 12/2014 | Seitz et al. |
| 2015/0065982 A1 | 3/2015 | Hamilton |
| 2015/0320613 A1 | 4/2015 | Seitz |
| 2015/0320621 A1 | 7/2015 | Seitz |
| 2015/0283004 A1 | 10/2015 | Seitz |
| 2015/0320611 A1 | 11/2015 | Seitz |
| 2015/0320612 A1 | 11/2015 | Seitz et al. |
| 2015/0320614 A1 | 11/2015 | Seitz |
| 2015/0320619 A1 | 11/2015 | Seitz |
| 2015/0320620 A1 | 11/2015 | Seitz |
| 2015/0320622 A1 | 11/2015 | Seitz |
| 2015/0328056 A1 | 11/2015 | Een et al. |
| 2016/0058627 A1 | 3/2016 | Barnes et al. |
| 2016/0095764 A1 | 4/2016 | Seitz |
| 2016/0100989 A1 | 4/2016 | Seitz |
| 2016/0100995 A1 | 4/2016 | Seitz |
| 2016/0100996 A1 | 4/2016 | Seitz |
| 2016/0100997 A1 | 4/2016 | Seitz |
| 2016/0100999 A1 | 4/2016 | Seitz |
| 2016/0136004 A1 | 5/2016 | LaVon et al. |
| 2017/0049637 A1 | 2/2017 | Mori et al. |
| 2017/0128285 A1 | 5/2017 | Seitz |

FOREIGN PATENT DOCUMENTS

| | | |
|---|---|---|
| EP | 1 695 742 | 8/2006 |
| EP | 1795163 A1 | 6/2007 |
| EP | 2314261 | 4/2011 |
| GB | 1 603 780 | 11/1981 |
| GB | 2245149 A | 1/1992 |
| JP | H01162802 A | 6/1989 |
| JP | H03202056 A | 9/1991 |
| JP | H11-21702 | 1/1999 |

(56) References Cited

FOREIGN PATENT DOCUMENTS

| | | |
|---|---|---|
| JP | 3046066 | 5/2000 |
| JP | 2003-285890 | 1/2002 |
| JP | 2002520090 A | 7/2002 |
| JP | 2003-070838 | 3/2003 |
| JP | 3386124 B2 | 3/2003 |
| JP | 2004-057640 | 2/2004 |
| JP | 2008253290 | 10/2008 |
| JP | 2009240694 A | 10/2009 |
| JP | 2011050484 A | 3/2011 |
| JP | 2011115229 A | 6/2011 |
| JP | 2014-508628 | 4/2014 |
| WO | WO-1999/055213 | 11/1999 |
| WO | 9960967 A1 | 12/1999 |
| WO | 9960974 A1 | 12/1999 |
| WO | WO-2000/027268 | 5/2000 |
| WO | WO-2002/014172 | 2/2002 |
| WO | 0232361 A2 | 4/2002 |
| WO | 02069866 A1 | 9/2002 |
| WO | WO 2005/039511 | 5/2005 |
| WO | 2005051263 A1 | 6/2005 |
| WO | 2007103097 A1 | 9/2007 |
| WO | WO2008123348 | 10/2008 |
| WO | 2008135870 A1 | 11/2008 |
| WO | 2015023561 A2 | 2/2015 |
| WO | 2015171378 A1 | 11/2015 |
| WO | 2015171382 A1 | 11/2015 |
| WO | 2016057777 A1 | 4/2016 |
| WO | 2016057857 A1 | 4/2016 |
| WO | 2016057858 A1 | 4/2016 |
| WO | 2017037958 A1 | 3/2017 |

OTHER PUBLICATIONS

Advertisements: "Introducing Pampers Phases", Sep. 1991.
"Introducing New! Luvs Phases", Jan. 1992.
"Introducing! The First Specially Designed Diaper Made Just For Your Walker", Sep. 1991.
"Dial-A-Wheel", Sep. 1991.
Photographs of Huggies Baby Steps Size 4 (1993).
Photographs of Huggies Baby Steps Size 3 (1990s).
Photographs of Huggies Baby Steps Size 4 (1991).
Photographs of Huggies Baby Steps Size 3 (1991).
Photographs of Huggies Ultratrim Size 4 (1992).
Photographs of Huggies Ultratrim Size 4 (1996).
Photographs of Huggies Ultratrim Size 2 SM/MED (1996).
Photographs of Huggies Ultratrim Size 1 Small (1996).
Photographs of Huggies Newborn (1996).
Photographs of Kleenex Newborn (1979).
Photographs of Kleenex (1980s).
Photographs of Pampers Custom Fit (2001).
Photographs of Pampers Phases Walker 2 (1993).
Photographs of Pampers Phases Infant 1 (1993).
Photographs of Pampers Phases Medium (1994).
Huggies Baby Steps Advertisement (copyrighted 1991).
International Search Report and Written Opinion, PCT/US2015/028173, dated Jul. 20, 2015.
All Office Actions, Responses and Claims, U.S. Appl. No. 14/309,158.
All Office Actions, Responses and Claims, U.S. Appl. No. 14/309,129.
All Office Actions, Responses and Claims, U.S. Appl. No. 14/680,186.
All Office Actions, Responses and Claims, U.S. Appl. No. 14/698,924.
All Office Actions, Responses and Claims, U.S. Appl. No. 14/698,968.
All Office Actions, Responses and Claims, U.S. Appl. No. 14/699,011.
All Office Actions, Responses and Claims, U.S. Appl. No. 14/805,601.
All Office Actions, Responses and Claims, U.S. Appl. No. 15/879,464.
All Office Actions, Responses and Claims, U.S. Appl. No. 14/699,097.
All Office Actions, Responses and Claims, U.S. Appl. No. 14/699,123.
All Office Actions, Responses and Claims, U.S. Appl. No. 14/805,673.
All Office Actions, Responses and Claims, U.S. Appl. No. 16/059,313.
All Office Actions, Responses and Claims, U.S. Appl. No. 14/699,145.
All Office Actions, Responses and Claims, U.S. Appl. No. 14/805,700.
All Office Actions, Responses and Claims, U.S. Appl. No. 16/022,885.
All Office Actions, Responses and Claims, U.S. Appl. No. 14/878,037.
All Office Actions, Responses and Claims, U.S. Appl. No. 14/809,324.
All Office Actions, Responses and Claims, U.S. Appl. No. 14/809,334.
All Office Actions, Responses and Claims, U.S. Appl. No. 14/878,142.
All Office Actions, Responses and Claims, U.S. Appl. No. 14/878,156.
All Office Actions, Responses and Claims, U.S. Appl. No. 14/996,683.
All Office Actions, Responses and Claims, U.S. Appl. No. 15/185,105.
All Office Actions, Responses and Claims, U.S. Appl. No. 15/267,742.
All Office Actions, Responses and Claims, U.S. Appl. No. 15/343,787.
All Office Actions, Responses and Claims, U.S. Appl. No. 16/023,487.
All Office Actions, Responses and Claims, U.S. Appl. No. 16/023,569.
All Office Actions, Responses and Claims, U.S. Appl. No. 16/023,766.
All Office Actions, Responses and Claims, U.S. Appl. No. 16/023,809.
All Office Actions; U.S. Appl. No. 17/738,341, filed May 6, 2022.
All Office Actions; U.S. Appl. No. 17/739,276, filed May 9, 2022.
All Office Actions; U.S. Appl. No. 17/851,633, filed Jun. 28, 2022.
Unpublished U.S. Appl. No. 17/738,341, filed May 6, 2022, to Bret Darren Seitz et al.
Unpublished U.S. Appl. No. 17/739,276, filed May 9, 2022, to Gary Dean Lavon et. al.
Unpublished U.S. Appl. No. 17/851,633, filed Jun. 28, 2022, to Gary Dean Lavon et al.

LENGTH-TO-SIDE SILHOUETTES OF ADULT DISPOSABLE ABSORBENT ARTICLES AND ARRAYS

CROSS REFERENCE TO RELATED APPLICATIONS

This application is a continuation of, and claims priority under 35 U.S.C. § 120 to, U.S. patent application Ser. No. 14/699,145, filed on Apr. 29, 2015, which claims the benefit, under 35 USC § 119(e), of U.S. Provisional Patent Application No. 61/990,365 filed on May 8, 2014, each of which are herein incorporated by reference in their entireties.

FIELD OF THE INVENTION

The present disclosure is directed to disposable absorbent articles and arrays of disposable absorbent articles which are designed to fit different adult body sizes, shapes and types, and as such are sized to fit a broad range of adult consumers.

BACKGROUND OF THE INVENTION

The Body Rise and Side Length are illustrated in FIG. 1. The relationship of the Body Rise to the Side Length (Body Rise-to-Side Length Ratio), as illustrated in FIG. 2, is an important product design parameter to ensure that the length of the article is not excessive. Excessive article length can result in extra materials in the crotch, leading to sagging, leakage, bulk and in material showing above the top of the clothing all of which can have a negative impact on performance and discretion.

The Body Length and Side Length are illustrated in FIG. 3. The Body Length-to-Side Silhouette, as illustrated in FIGS. 4 and 5 correlates with the Body Rise-to-Side Length Ratio as the values of both increase as BMI and Waist Circumference increase. This is shown in FIGS. 2, 4, and 5.

As the Waist Circumference increases with BMI, Body Rise-to-Side Length Ratio and Body Length-to-Side Silhouette both increase. A key benefit of having the Product Length-to-Side Silhouette closer to that of the Body Length-to-Side Silhouette and designed to change accordingly with BMI and Waist Circumference is that the product itself more closely matches the shape of the body. This results in the product being deformed to a significantly lesser degree during application than one that is generically designed to fit a bigger range as illustrated by the current marketed products. It also results in a product fit, which is more tailored to the body shape, providing more effective gasketing, product coverage and less extraneous material in the crotch. In fact, many of the current marketed products are designed to fit increments as large as 100 pounds and, as such do not provide adequate fit, gasketing, comfort, coverage and discretion across the entire range. Additionally, product designs which mimic the general shape of the body convey to consumers a better, more tailored fit as the Product Length-to-Side Silhouettes are more similar to consumers' Body Length-to-Side Silhouettes. The designs enabled by the present disclosure are more targeted by design and therefore provide a greater level of fit, gasketing, coverage, comfort and discretion.

Adult incontinence ("AI") absorbent articles of the present disclosure may be used to absorb and contain liquid and other discharges from the human body to prevent the body and clothing from becoming soiled. For adults who suffer from urinary incontinence, urine voiding consists of two general types: stress urinary incontinence ("SUI") and urge urinary incontinence ("UUI"). SUI is caused by high pressure on the bladder induced by coughing, sneezing, laughing, bending, etc., and can result in a high flow rate though at a smaller urine volume that is associated with UUI. UUI can result in a full bladder release, though at a lower flow rate than that associated with SUI.

Adult Incontinence articles come in a variety of designs, each typically available in multiple sizes, including 2, 3 and 4 size arrays. The size of articles of the prior art typically affects, for example, the size of the waist opening, the size of the openings around the thighs, and the length or "pitch" of the article. Many of these prior art articles are designed to fit ranges up to 100 pounds. The prior art articles are typically sized and sold by waist circumference dimension. The various sizes can have a range in waist circumference of as much as 12 inches and in some cases up to 16 inches. If a consumer selects an adult incontinence article of the prior art which is size appropriate based on the waist circumference dimension of the wearer given the large ranges associated with the various sizes, the thigh openings or pitch of the article, for instance, may be too large for proper fit on the wearer, potentially leading to slipping, sliding, sagging, drooping, or a loss of gasketing effects that are designed to inhibit leakage. Alternatively, depending on where the wearer is within the large size range, the thigh opening or pitch of the article may be too small for proper fit, potentially leading to wearer discomfort, skin marking of the wearer's skin or improper application or positioning of the article on the wearer.

Desirably, an adult absorbent article should be designed and sized to maintain contact with and conform as closely as possible to a wearer's body. Such a body-conforming design may increase the effectiveness of the adult absorbent article by reducing the possibility that urine, or the like, will spread or travel along the wearer's body and leak out of rather than be absorbed into the adult absorbent article. However, current adult absorbent articles on the market do not adequately address body shape or product shape and therefore do not fit a broad range of users adequately or provide the desired level of close fit. Typically AI packages of adult absorbent articles are labeled with a recommended wearer waist circumference range that the packaged article is intended to fit. As a result, the waist circumference is often the sole criteria used to identify the size of an AI article. The waist size does not in itself adequately describe the body shape of the individual and therefore does not help define the hip or thigh circumference nor the pitch that may be needed to provide the proper fit, comfort, coverage and gasketing of the article. This is the case even though other characteristics and anthropometric attributes of potential wearers (for example, age, height, weight, thigh circumference, and rise) may vary widely within the recommended waist circumference range, and may result in an ill-fitting article even though a wearer's waist circumference falls within that range. There is a need for adult absorbent articles that conform well to various wearers' body shapes and sizes. While there is a wide range of body shapes and sizes among women, available products do not reflect this wide range; rather, absorbent articles available today within a given product array tend to be scaled versions of each other, and do not even follow the natural trend of body shape and dimensional changes across the range of consumers, i.e. smaller to larger women as well as women of varying shape.

Body Mass Index (BMI) is on the rise globally for both men and women. In the U.S. alone, more than ⅓ of adult females are now considered obese (BMI>30). This has changed significantly over the past 30 years; in 1980 only about 16% of U.S. adult females were obese. Larger women exhibit different ratios of body anthropometrics than smaller women, i.e., all body dimensions do not simply scale-up as women get larger. In addition, women across the range of BMI may also have very different body shapes. There is a lack of recognition and understanding of this issue by current adult absorbent article manufacturers and as such consumers' needs are not being adequately met. Therefore, there is a need to develop adult absorbent articles for a wide variety of body shapes and sizes in order to provide an improved level of fit and contact between the body and the adult absorbent article to reduce the occurrence leakage and improve the overall fit, comfort, coverage and discretion of the article. There is a clear need for adult absorbent articles which are designed for variety of wearers based on their BMI and body shape. There is also a need to communicate to wearers the benefits of such customized adult absorbent articles in an easy-to-understand manner (e.g., some women may not understand what BMI is or know their BMI number), which is not off-putting (e.g., without stigmatizing or embarrassing women based on their BMI).

These are all objects of the present disclosure; embodiments of the present disclosure may combine various objects mentioned. A particular embodiment may, but need not, embody every object as described.

SUMMARY OF THE DISCLOSURE

In one embodiment, an array of packages may comprise two or more different sizes of disposable absorbent articles. The array may comprise first and second packages comprising first and second disposable absorbent articles. Each of the first and second absorbent articles may comprise a topsheet, backsheet, absorbent core and a pair of side seams. The first absorbent article may be a first size and may be in a closed form. The second absorbent article may be a second size and may also be in a closed form. The second absorbent article may have one or more of (a) larger Relaxed Product Side Length (303) than the first absorbent article or (b) a larger Relaxed Product Length (300) than the first absorbent article. The Product Length-to-Side Silhouette of the second absorbent article may be equal to or greater than a Product Length-to-Side Silhouette of the first absorbent article. And, the first and second packages may comprise the same brand name and/or sub-brand name.

In another embodiment, an array of packages may comprise two or more different sizes of disposable absorbent articles. The array may comprise first and second packages comprising first and second disposable absorbent articles. Each of the first and second absorbent articles may comprise a topsheet, backsheet, absorbent core and a pair of side seams. The first absorbent article may be a first size and may be in a closed form. The second absorbent article may be a second size, different from the first size, and may also be in a closed form. An Array Average Product Length-to-Side Silhouette of the first and second packages may be from about 1.2 to about 1.6. And, the first and second packages may comprise the same brand name and/or sub-brand name.

In another embodiment, an adult incontinence disposable absorbent article may have a Product Waist-to-Side Silhouette from 1.2 to about 1.5. And, the adult incontinence disposable absorbent article may be closed form.

In a fourth embodiment, an On-Line Array of packages may comprise two or more different sizes of disposable absorbent articles. The array may comprise first and second packages comprising first and second disposable absorbent articles. Each of the first and second absorbent articles may comprise a topsheet, backsheet, absorbent core and a pair of side seams. The first absorbent article may be a first size and may be in a closed form. The second absorbent article may be a second size and may also be in a closed form. The second absorbent article may have one or more of (a) larger Relaxed Product Side Length (303) than the first absorbent article or (b) a larger Relaxed Product Length (300) than the first absorbent article. The Product Length-to-Side Silhouette of the second absorbent article may be equal to or greater than a Product Length-to-Side Silhouette of the first absorbent article. And, the first and second packages may comprise the same brand name and/or sub-brand name.

DETAILED DESCRIPTION OF THE INVENTION

"Pull-on garment" or "pant" means articles of wear which have a defined waist opening and a pair of leg openings and which are pulled onto the body of the wearer by inserting the legs into the leg openings and pulling the article up over the waist.

"Disposable" means garments, which are not intended to be laundered or otherwise restored or reused as a garment (i.e., they are intended to be discarded after a single use and to be recycled, composted or otherwise disposed of in an environmentally compatible manner). The pull-on garment may be "absorbent" such that it absorbs and contains the various exudates discharged from the body.

Figure 15:
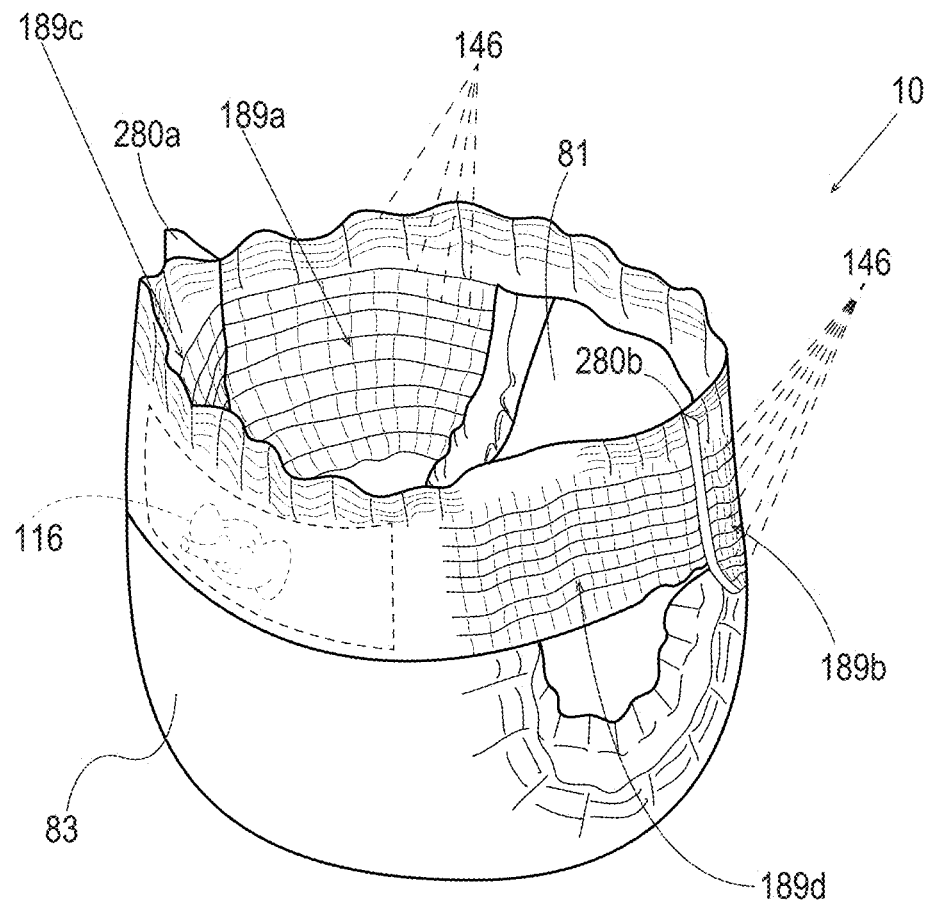
FIG. 15 is a perspective view the pant diaper shown in FIG. 12 wherein belts connect opposing waist regions.
Figure 16:
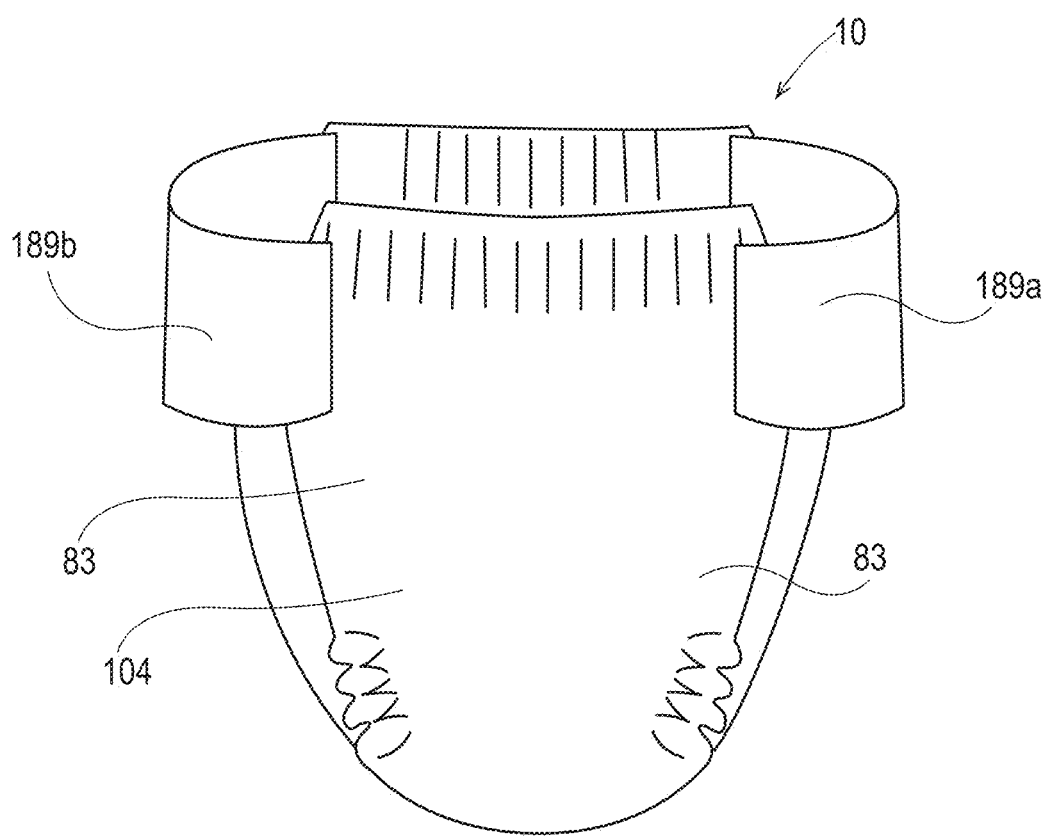
FIG. 16 is a perspective view the pant diaper shown in FIG. 13 wherein flaps connect opposing waist regions.
Figure 17:
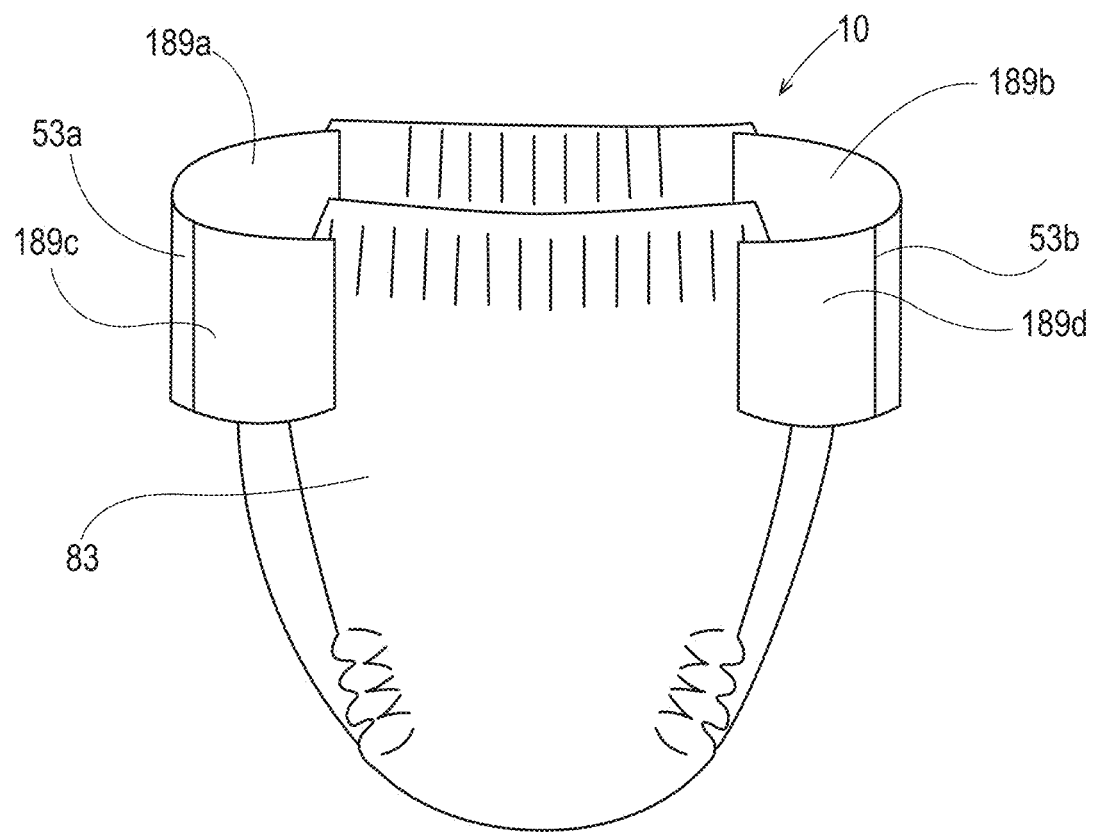
FIG. 17 is a perspective view the pant diaper shown in FIG. 14 wherein side seams connect the flaps and opposing waist regions.

"Closed form" means opposing waist regions are joined to form a continuous waist opening and leg openings. See FIGS. 15-17.

"Array" means a display of packages comprising disposable articles of different sizes having like article constructions (e.g., same elastomeric materials [compositionally and/or structurally] in the flaps, graphic elements) said packages having the same brand and/or sub-brand, and said packages oriented in proximity to each other in a given area of a retail store. An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Depend," and same sub-brand, for example, "for Women Underwear." A different array may have the brand "Depend" and the sub-brand "Silhouette For Women." The differences between the "for Women Underwear" array and the "Silhouette For Women" arrays include different elastomeric materials in the side flaps, where "for Women Underwear" comprises strands as the elastomeric material and "Silhouette For Women" comprises a film elastomeric material." Furthermore, the packaging is distinctly different in that "for Women Underwear" is packaged in a predominately green, film bag and "Silhouette For Women" is packaged in a predominately maroon box.

Further regarding "Arrays," as another example of two separate "arrays" having the same brand, "Certainty," one line-up has the sub-brand "Women's Underwear." A different array may have the same brand "Certainty" and the sub-brand "Smooth Shape Briefs for Women." The differences between the "Women's Underwear" array and the "Smooth Shape Briefs for Women" arrays include different elastomeric materials in the side flaps, where "Women's Underwear" comprises strands as the elastomeric material and "Smooth Shape Briefs for Women" comprises a film elastomeric material." Furthermore, the packaging is distinctly different in that "Women's Underwear" is packaged in a predominately blue, film bag and "Smooth Shape Briefs for Women" is packaged in a predominately maroon box.

Arrays also often have the same trademarks, including trademarks of the brand, sub-brand, and/or features and/or benefits across the line-up.

"On-line Array" means an "Array" distributed by a common on-line source.

Figure 1:
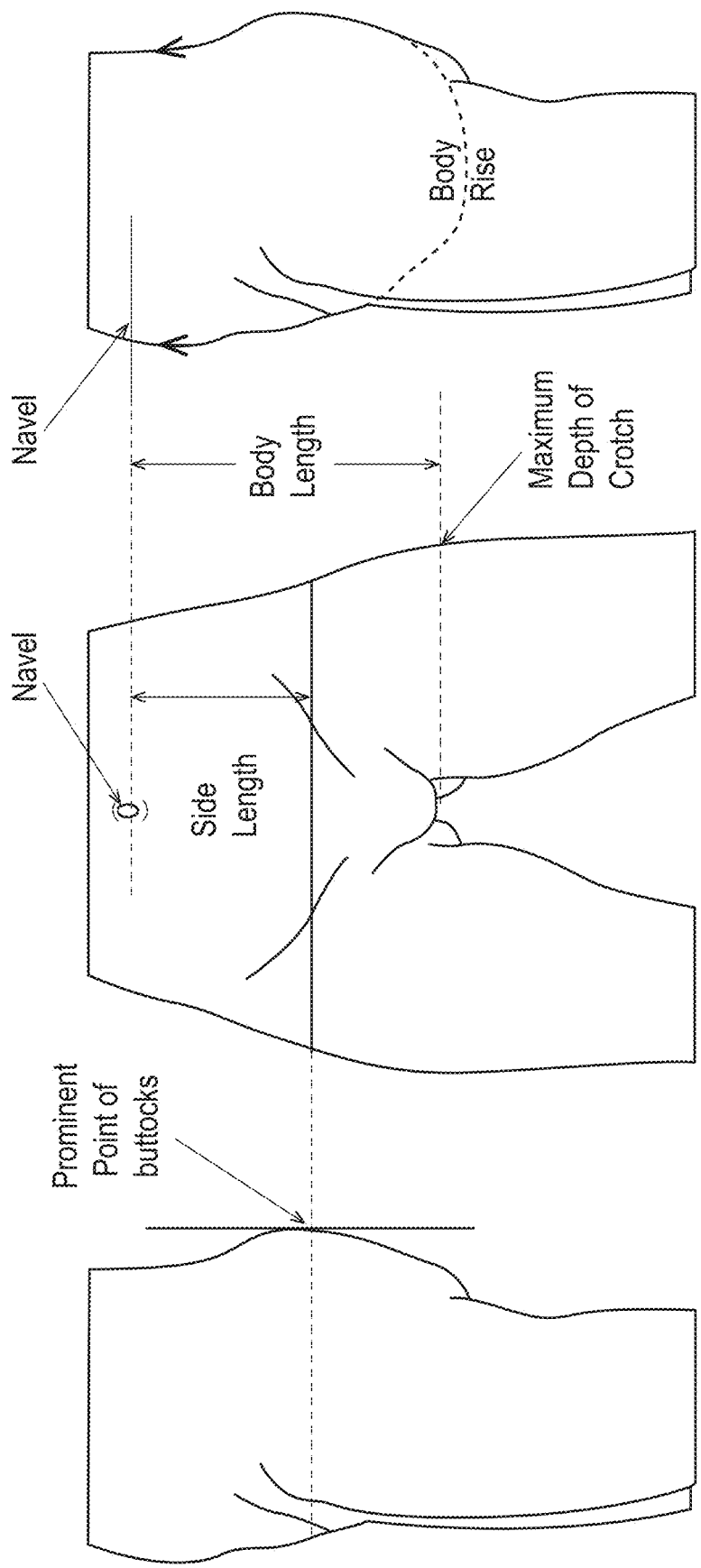
FIG. 1 shows Body Rise and Side Length against a female body shape.
Figure 2:
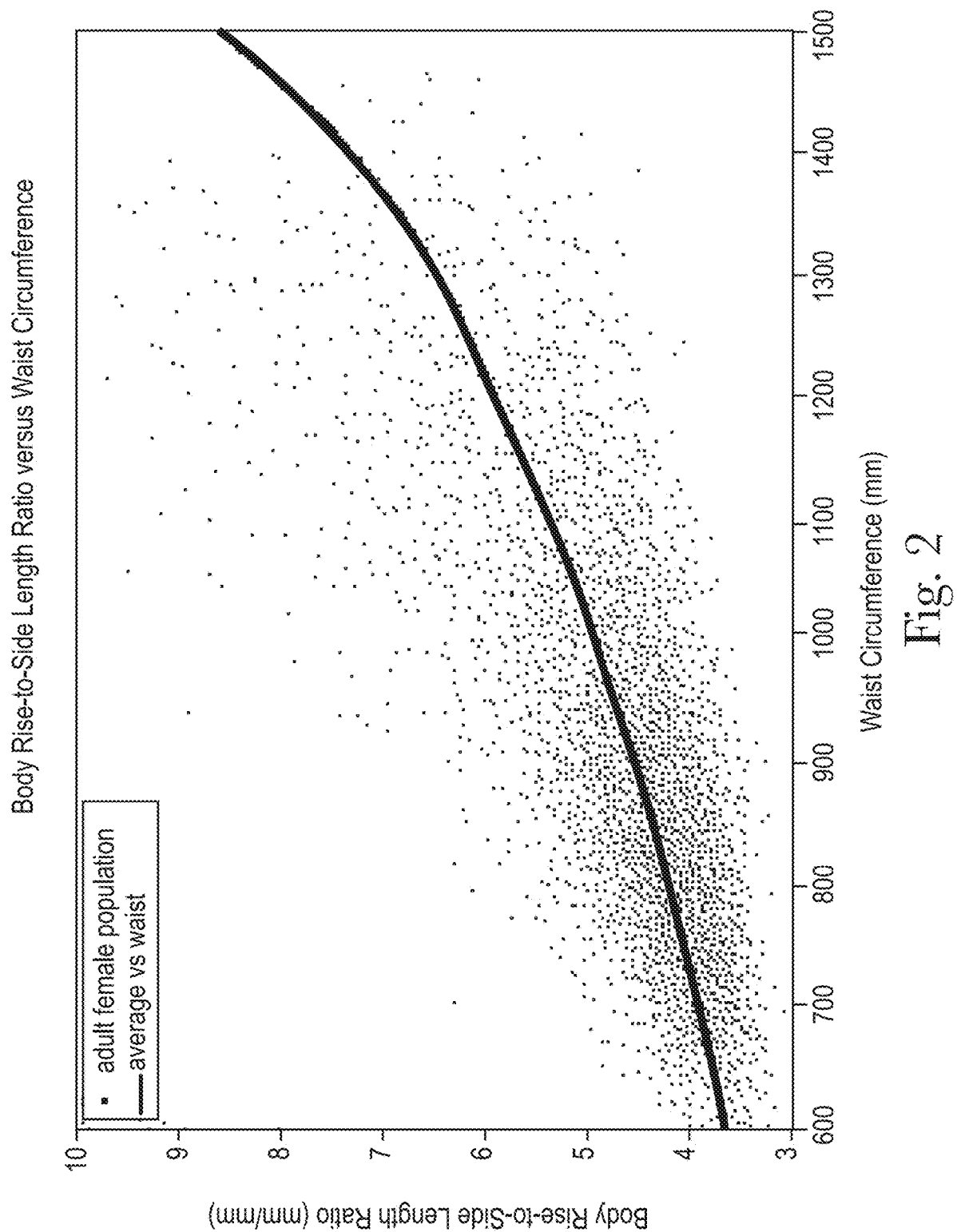
FIG. 2 is a chart which shows how the average ratio of Body Rise-to-Side Length Ratio changes as Waist Circumference increases.

"Body Rise" means the surface distance from omphalion (center of navel) to the subjects back at the level of the navel measured through the crotch and over the middle of the buttock. See FIG. 1.

Figure 3:
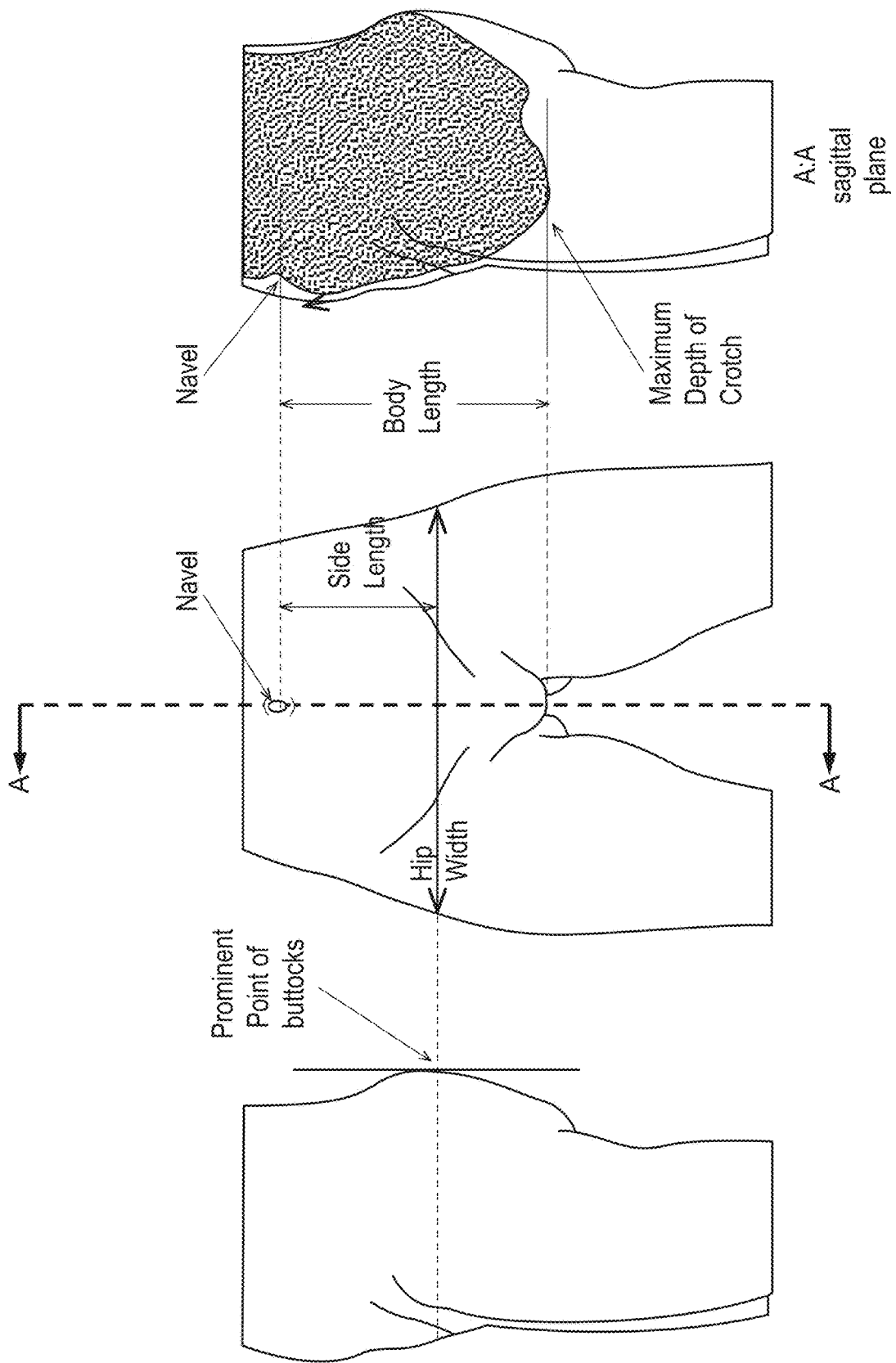
FIG. 3 shows Body Length and Side Length against a female body shape.

"Body Length" means the vertical distance from the navel to the maximum depth of the crotch, determined by the maximum depth of the crotch within the sagittal plane. See FIG. 3.

"Side Length" means the vertical distance from the navel to the level of the hip (where the hips are defined at the maximum prominent point of the buttocks as seen from the side. See FIG. 3.

"Body Rise-to-Side Length Ratio" means the Body Rise (mm) divided by the Side Length (mm). See FIG. 1.

"Body Length-to-Side Silhouette" means the Body Length (mm) divided by the Side Length (mm). See FIG. 3.

"Product Length-to-Side Silhouette" means Relaxed Product Length (300) (mm) divided by the Relaxed Product Side Length (303) (mm). See FIG. 6.

"Array Average Product Length-to-Side Silhouette" means the average Product Length-to-Side Silhouette of each size offered in a product array. For example, the Depend Underwear for Women (Maximum Absorbency) is marketed and sold in an array of 3 sizes: Small/Medium; Large and Extra Large. The Array Average Product Length-to-Side Silhouette is the average of: The Product Length-to-Side Silhouette for size Small/Medium; the Product Length-to-Side Silhouette for size Large; and the Product Length-to-Side Silhouette for size Extra Large. Table 1 shows examples of the Product Length-to-Side Silhouette for some currently marketed product arrays.

Figure 6:
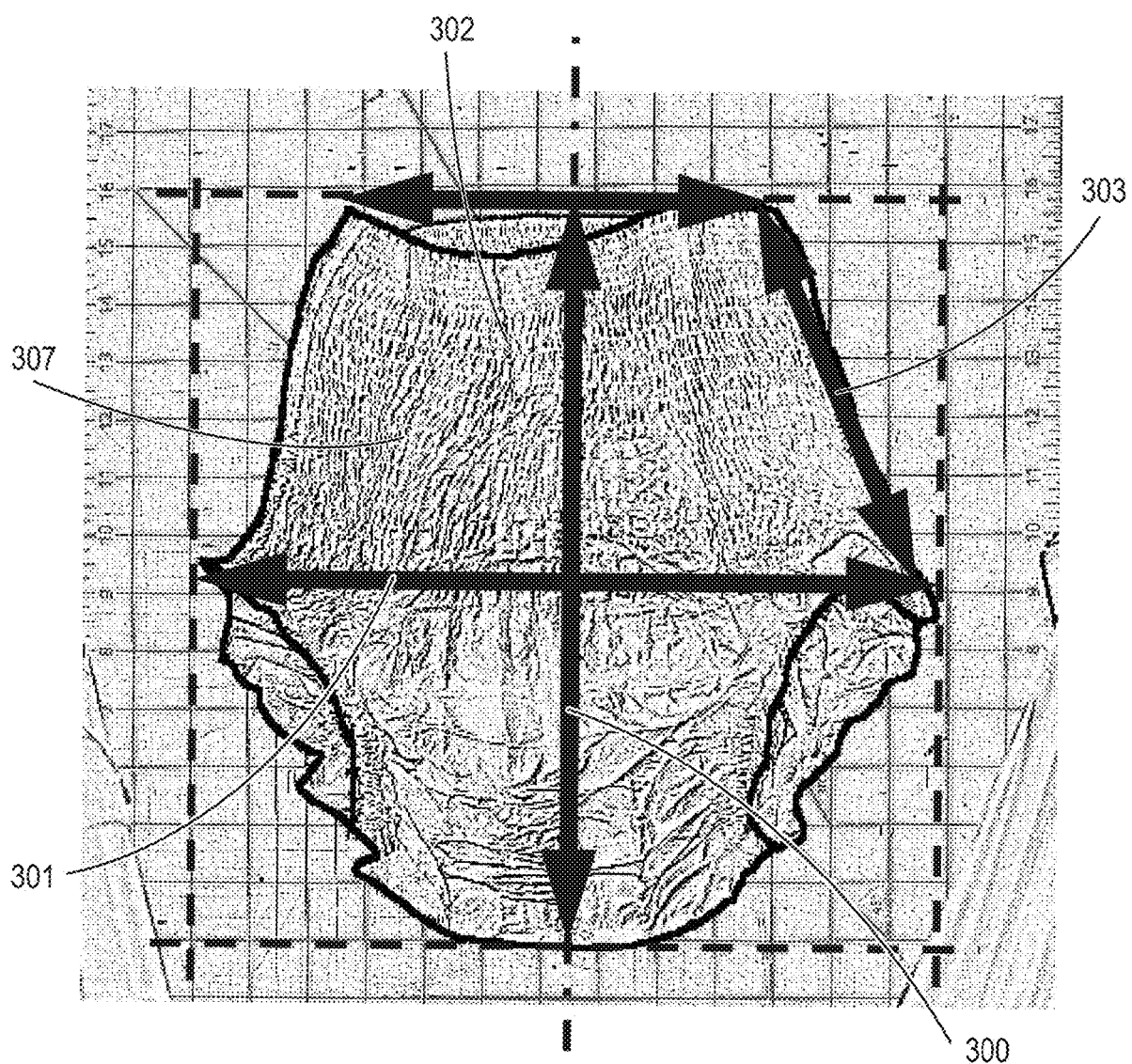
FIG. 6 shows an AI pant product in its laid out, relaxed, and unfolded state.

"Relaxed Product Length" means the longitudinal distance between the longitudinally distal most point in the crotch region and the longitudinally distal most point along the front waist edge. The longitudinal distance is measured parallel to the longitudinal axis of the product. Refer to FIG. 6.

"Relaxed Product Hip Width" means the lateral distance from the laterally distal most point of the left side edge of the product at the upper edge of the left leg opening to the laterally distal most point of the right side edge of the product at the upper edge of the right leg opening. Refer to FIG. 6. The lateral distance is measured perpendicular to the longitudinal axis of the product.

"Relaxed Product Waist Width" means the lateral distance from the distal most point at the right side of the front waist edge to the distal most point at the left side of the front waist edge. The lateral distance is measured perpendicular to the longitudinal axis of the product. Refer to FIG. 6.

"Relaxed Product Side Length" means the linear distance from the point of intersection between the waist edge and the side edge of the product to the point of intersection between the top of the leg opening and the same side edge of the product. The relaxed product side length measurement is the average of the measurements from the left and right sides of the product. Refer to FIG. 6.

"Target Waist Range" means the waist range as defined on each product package. For example, the Depend for Women Moderate Absorbency S/M package indicates a waist of 28-40 in (71-102 cm).

"Average Targeted Waist" means the average of the Target Waist Range. For example, the Depend for Women Moderate Absorbency S/M has a Target Waist Range (as defined on its package) of 71-102 cm. The Average Targeted Waist for this product is 86.5 cm.

Consumers who are urinary incontinent often are traumatized by the condition. Many aspects of the condition contribute to the trauma, like the fear of having an incontinent event in public. Even when wearing an absorbent article, there is still the fear of leaking, and the fear of her absorbent article being noticeable under her clothes. As such providing a product experience that helps normalize the condition by providing a more underwear-like, thin and body conforming structure across the entire BMI range is one of the objects of the present disclosure.

The body mass index (BMI) is a classification system for body shapes based upon height and mass. BMI may be calculated as follows:

$$BMI = \frac{\text{weight(kg)}}{\text{height(m)}^2} = \frac{703 * \text{weight(lb)}}{\text{height(in)}^2}$$

The BMI comprises different classes of body mass, including: underweight (BMI<20), normal weight (BMI 20-25), overweight (BMI 25-30), obese (BMI 30-40), and morbidly obese (BMI>40).

Figure 7:
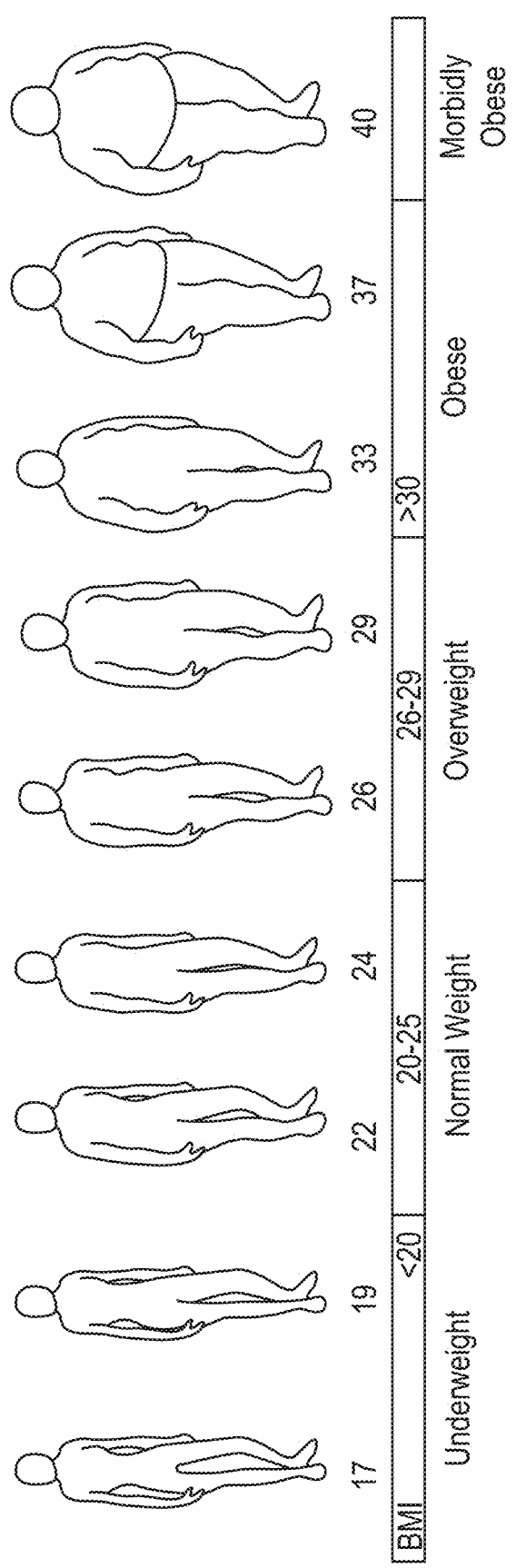
FIG. 7 shows how the general female body shape changes as BMI increases.
Figure 8:
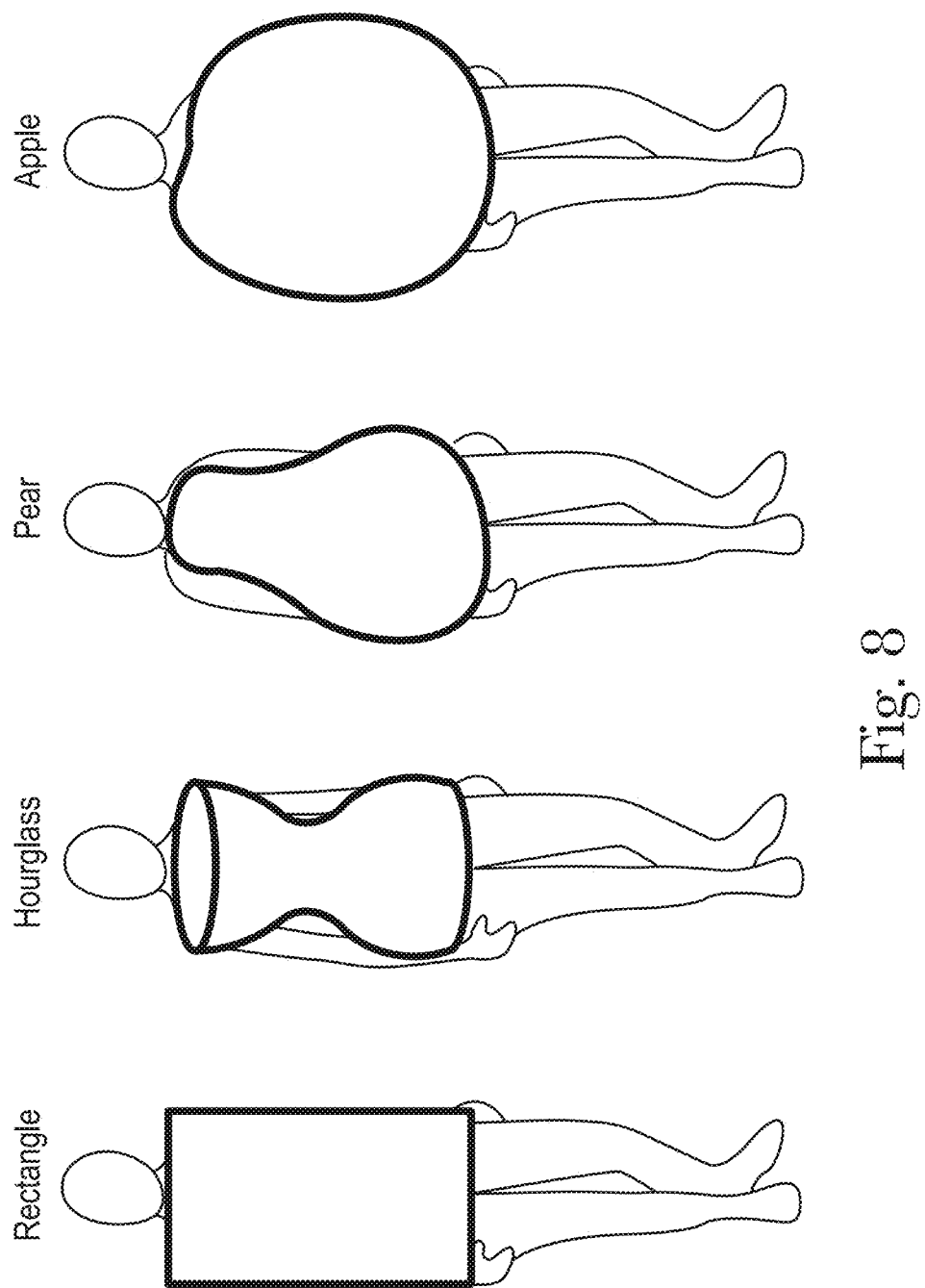
FIG. 8 depicts the variability of female body shapes within each BMI class.

FIG. 7 illustrates how the general female body shape changes as BMI increases. FIG. 8 illustrates a variety of specific shapes that may exist within each BMI class: rectangle (also known as cylindrical), hourglass, pear, and apple. The higher her BMI, the further to the right (toward the apple) a women typically is on this body shape scale. The prevalence of these shapes differs among BMI ranges, for instance, higher BMI women have a higher probability of being apple or pear shaped. Adult absorbent articles may be marketed to women of a particular body shape, such as apple, rather than focusing on exact BMI values (which may be off-putting to a consumer), in order to match a wearer with the article that will best fit her unique body shape or size.

Figure 4:
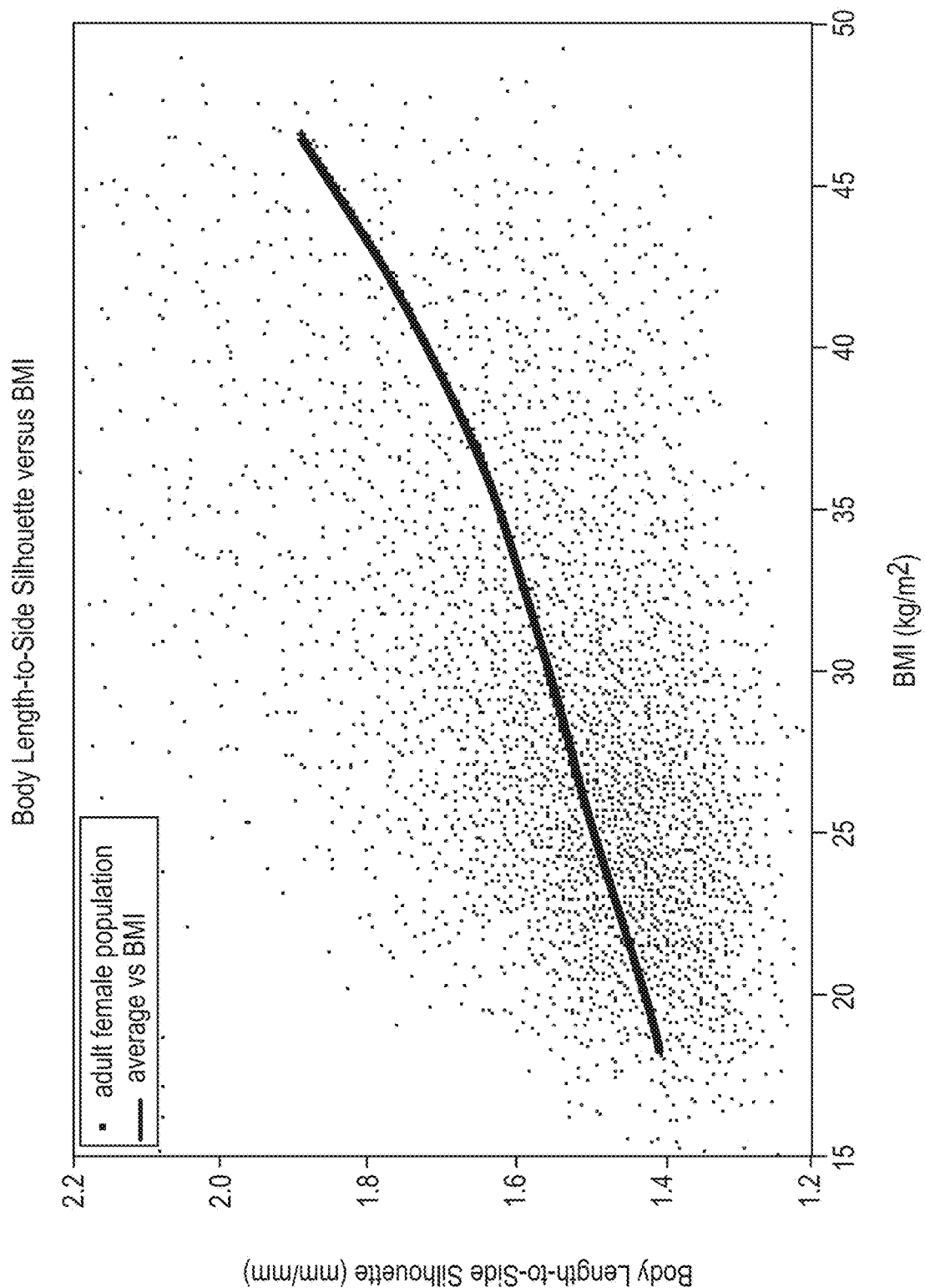
FIG. 4 is a chart which shows how the average Body Length-to-Side Silhouette changes as BMI increases.
Figure 5:
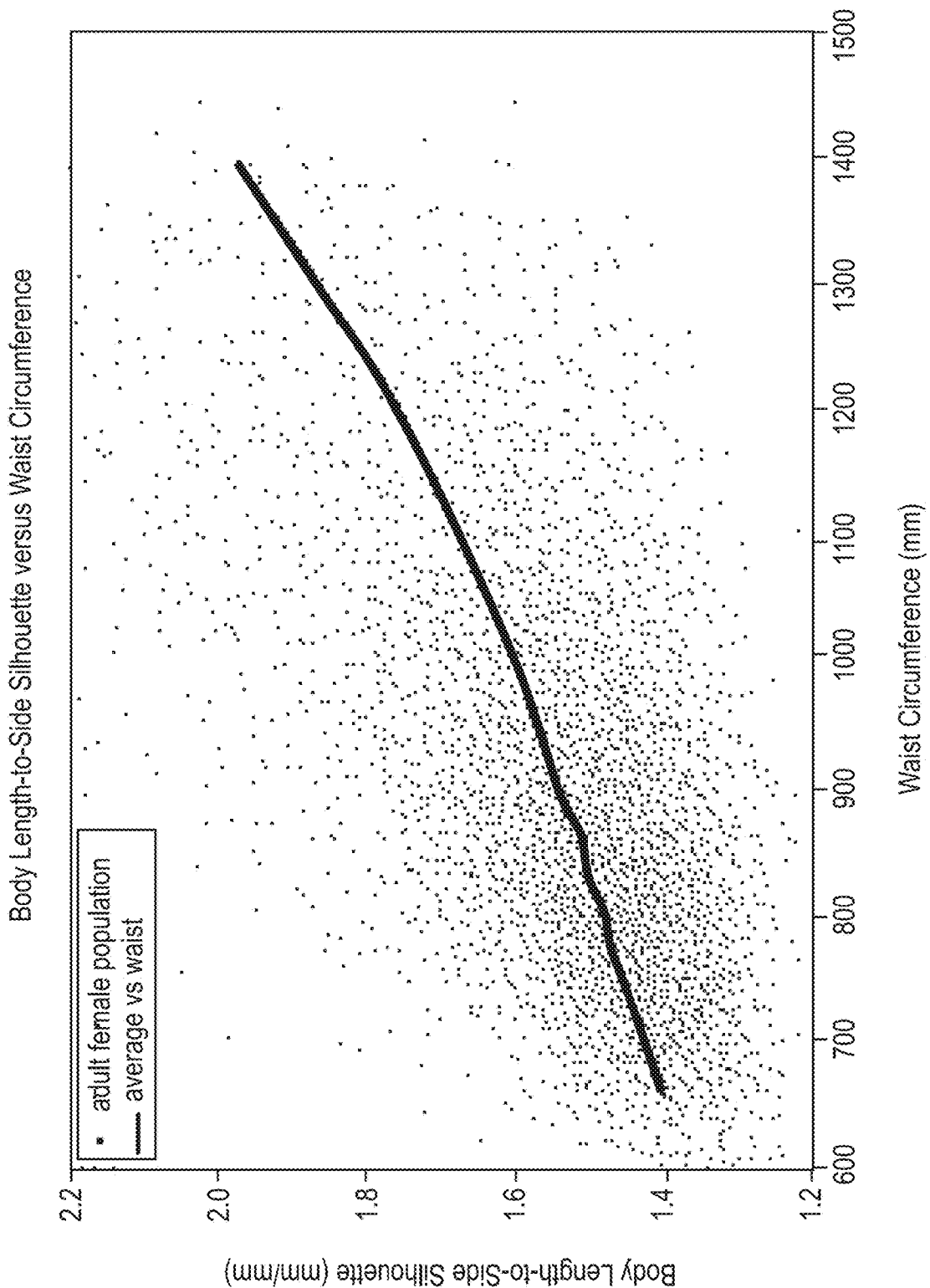
FIG. 5 is a chart which shows how the average Body Length-to-Side Silhouette changes as waist circumference increases.

One region where the shape of the female body changes as BMI gets higher is in the Body Length-to-Side Silhouette. The Body Length-to-Side Silhouette gets larger on average for larger women. FIGS. 4 and 5 illustrate how the Body Length-to-Side Silhouette changes as both BMI and Waist Circumference gets larger.

It may be desirable to link the Product Length-to-Side Silhouette to that of the targeted consumers Body Length-to-Side Silhouette in order to achieve a better fitting, better conforming, better gasketing product. This may increase the wearing comfort for each consumer while reducing leakage. Additionally, a product array where the Product Length-to-Side Silhouette of each subsequently larger size follows the same general trend as the Body Length-to-Side Silhouette for each subsequently larger size may also deliver a better fitting, better conforming article to each consumer regardless of their respective BMI.

Figure 9:
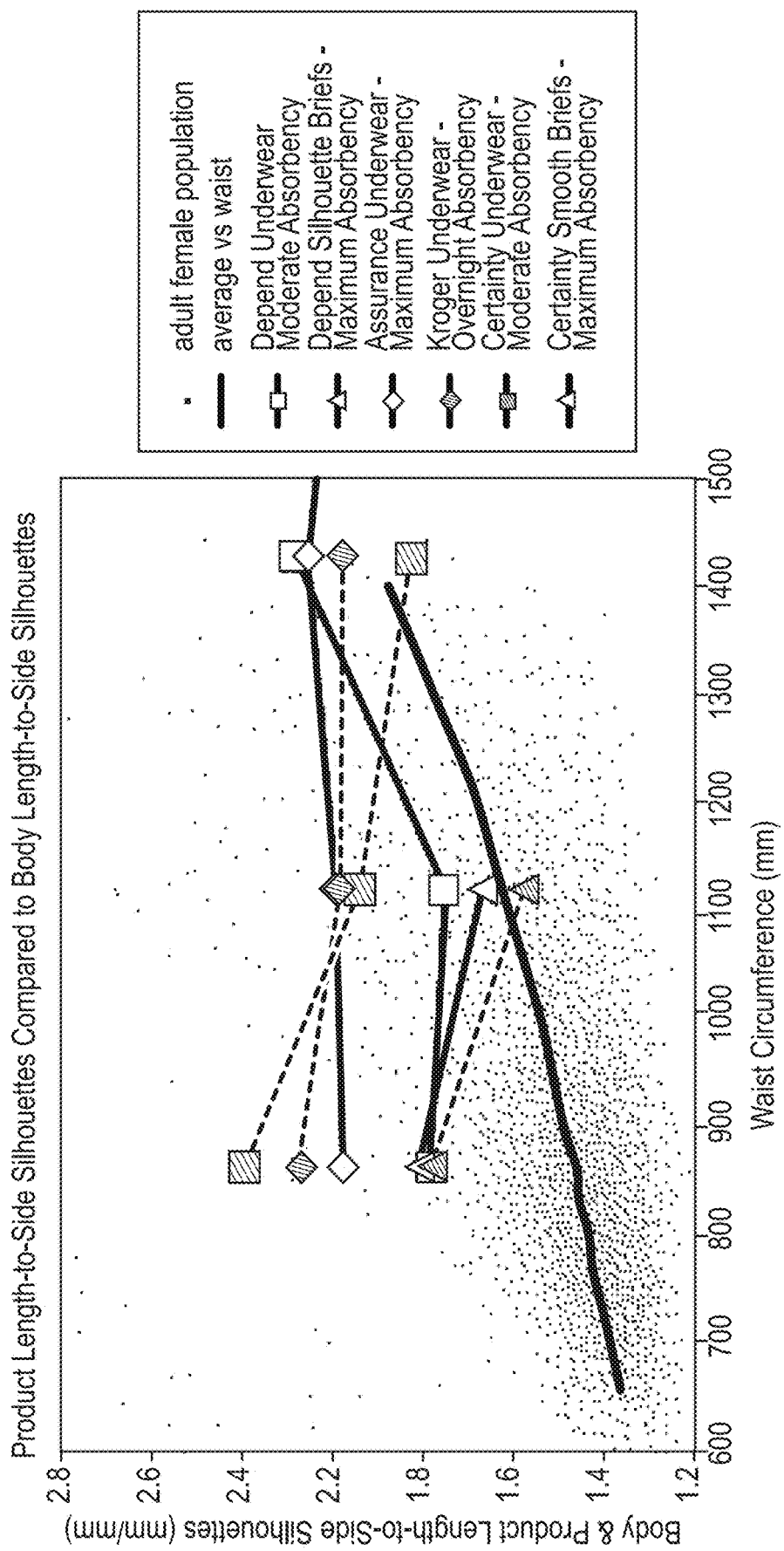
FIG. 9 is a chart which shows examples of existing product arrays, and how their Product Length-to-Side Silhouettes compare to the Body Length-to-Side Silhouettes of the waist circumferences of the consumers each product is targeted to fit.

While today's AI product arrays are not targeted toward the consumer's BMI, they are targeted toward their Waist Circumference. Table 1 details some of today's marketed product arrays ("comparative example arrays" or "existing product arrays"). FIG. 9 shows how the Product Length-to-Side Silhouettes of these arrays compare to the consumers' Body Length-to-Side Silhouettes. It can be seen that for these comparative example arrays, their Product Length-to-Side Silhouettes not only fail to match those of their target consumers, but it can also be seen that the trend from size to size for the existing product arrays is that the Product Length-to-Side Silhouettes get smaller rather than larger as do the Body Length-to-Side Silhouettes of the consumers. The result of this mismatch is that the products provide an inferior level of fit, comfort, coverage and gasketing across much of the BMI range than products that are designed in line with the anthropometric measures across the same BMI range.

TABLE 1

Examples of Product Length-to-Side Silhouettes for Existing Product Arrays

|  | Minimum Waist Target (mm) | Maximum Waist Target (mm) | Average Targeted Waist (mm) | Relaxed Product Length (mm) | Relaxed Product Side Length (mm) | Product Length-to-Side Silhouette (mm/mm) | Array Average Product Length-to-Side Silhouette (mm/mm) |
|---|---|---|---|---|---|---|---|
| Depend for Women Underwear Moderate Absorbency |  |  |  |  |  |  |  |
| size S/M | 710 | 1020 | 865 | 335 | 179 | 1.867 |  |
| size L | 970 | 1270 | 1120 | 371 | 202 | 1.834 | 1.969 |
| size XL | 1220 | 1630 | 1425 | 385 | 175 | 2.205 |  |
| Depend Silhouette for Women Briefs Maximum Absorbency |  |  |  |  |  |  |  |
| size S/M | 710 | 1020 | 865 | 312 | 164 | 1.896 | 1.819 |
| size L/XL | 970 | 1270 | 1120 | 366 | 210 | 1.741 |  |
| Women's Assurance Underwear Maximum Absorbency |  |  |  |  |  |  |  |
| size S/M | 710 | 1020 | 865 | 312 | 149 | 2.087 |  |
| size L | 970 | 1270 | 1120 | 346 | 165 | 2.103 | 2.102 |
| size XL | 1220 | 1630 | 1425 | 349 | 161 | 2.173 |  |
| size 2XL* | 1730 | 2030 | 1880 | 452 | 221 | 2.043 |  |
| Kroger Overnight Underwear Overnight Absorbency |  |  |  |  |  |  |  |
| size S/M | 710 | 1020 | 865 | 314 | 143 | 2.191 |  |
| size L | 970 | 1270 | 1120 | 359 | 171 | 2.097 | 2.124 |

TABLE 1-continued

Examples of Product Length-to-Side Silhouettes for Existing Product Arrays

|  | Minimum Waist Target (mm) | Maximum Waist Target (mm) | Average Targeted Waist (mm) | Relaxed Product Length (mm) | Product Side Length (mm) | Product Length-to-Side Silhouette (mm/mm) | Array Average Product Length-to-Side Silhouette (mm/mm) |
|---|---|---|---|---|---|---|---|
| size XL Certainty Women's Underwear Moderate Absorbency | 1220 | 1630 | 1425 | 359 | 172 | 2.084 | |
| size S/M | 710 | 1020 | 865 | 319 | 137 | 2.330 | |
| size L | 970 | 1270 | 1120 | 360 | 176 | 2.046 | 2.099 |
| size XL Certainty Smooth Shape Briefs for Women Maximum Absorbency | 1220 | 1630 | 1425 | 335 | 174 | 1.919 | |
| Certainty Maximum S/M | 710 | 1020 | 865 | 318 | 170 | 1.866 | 1.752 |
| Certainty Maximum L/XL | 970 | 1270 | 1120 | 345 | 211 | 1.639 | |

*product not shown in chart on FIG. 9.

Figure 10:
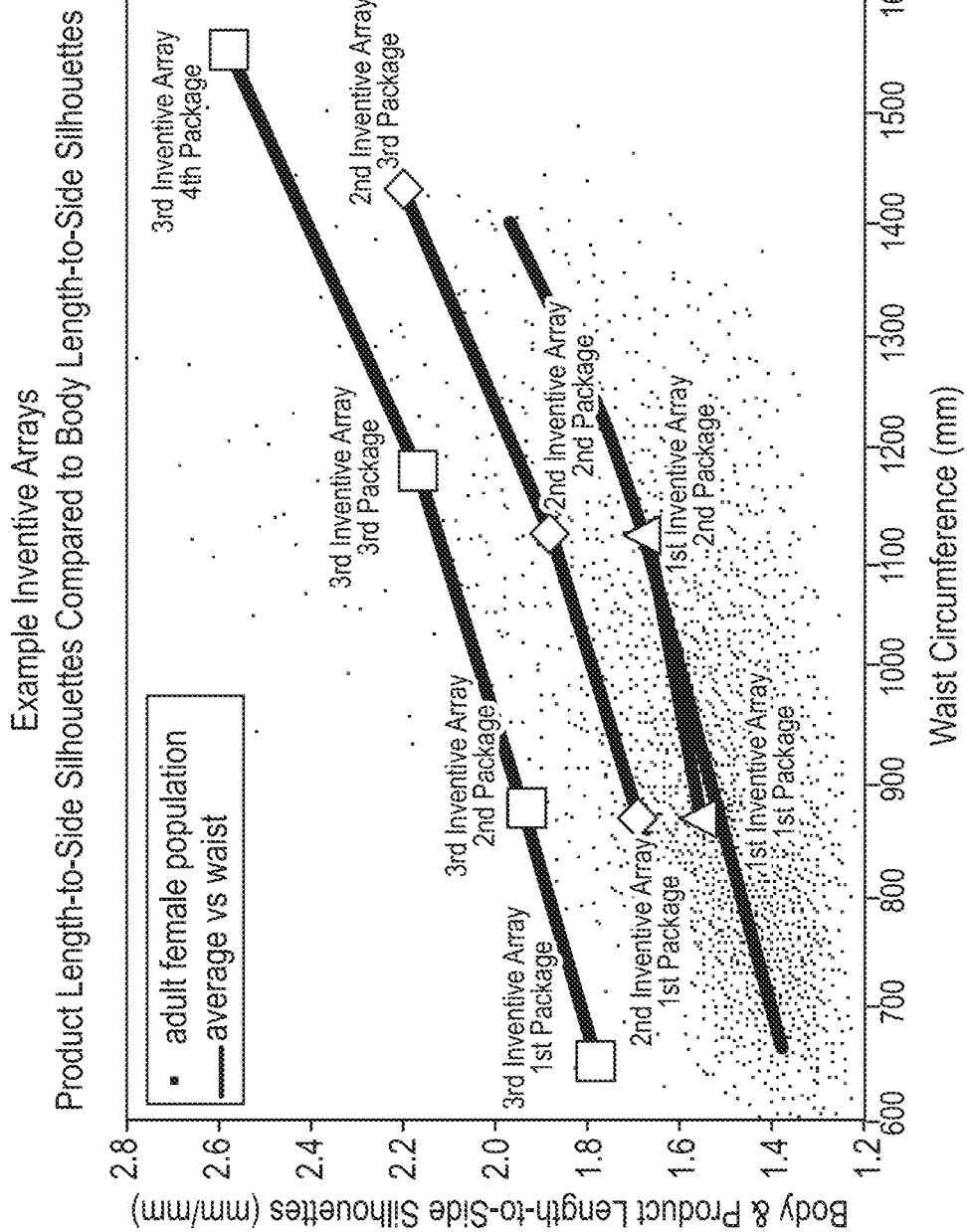
FIG. 10 is a chart which shows examples of inventive product arrays, and how their Product Length-to-Side Silhouettes compare to the Body Length-to-Side Silhouettes of the waist circumferences of the consumers each product is targeted to fit.
Figure 11:
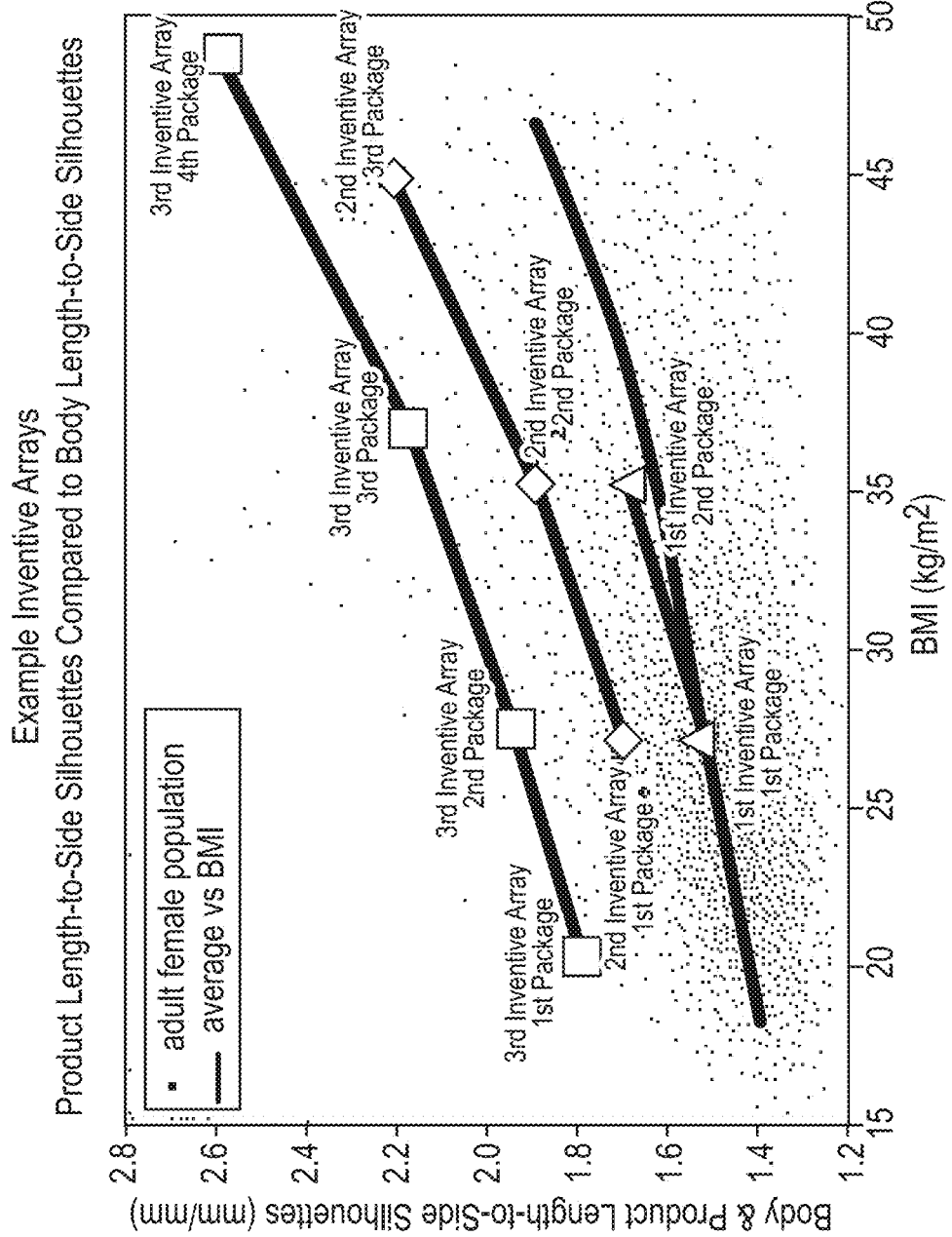
FIG. 11 is a chart which shows examples of inventive product arrays, and how their Product Length-to-Side Silhouettes compare to the Body Length-to-Side Silhouettes of the BMI of the consumers each product is targeted to fit.

Table 2 below illustrates several inventive arrays of 2, 3, and 4 packages, whose Product Length-to-Side Silhouettes match the trends of the consumers that they are targeted to fit and thereby provide better fit & comfort while reducing the chance of leakage. These inventive arrays are provided simply as non-limiting examples. Other inventive arrays are possible within the scope of this disclosure. These inventive arrays are also shown in FIGS. 10 and 11.

TABLE 2

Examples of Inventive Product Arrays

|  | Target Waist Range (mm) | Average Targeted Waist (mm) | Target BMI Range | Average Targeted BMI | Relaxed Product Length (mm) | Product Side Length (mm) | Product Length-to-Side Silhouette (mm/mm) | Array Average Product Length-to-Side Silhouette (mm/mm) |
|---|---|---|---|---|---|---|---|---|
| 1st Inventive Array (2 package array) | | | | | | | | |
| 1st Package in Array | 710-1020 | 865 | 22-32 | 27 | 210 | 137 | 1.531 | 1.612 |
| 2nd Package in Array | 970-1270 | 1120 | 31-40 | 35 | 258 | 152 | 1.693 | |
| 2nd Inventive Array (3 package array) | | | | | | | | |
| 1st Package in Array | 710-1020 | 865 | 22-32 | 27 | 233 | 137 | 1.700 | |
| 2nd Package in Array | 970-1270 | 1120 | 31-40 | 35 | 288 | 152 | 1.892 | 1.931 |
| 3rd Package in Array | 1220-1630 | 1425 | 38-51 | 45 | 352 | 160 | 2.201 | |
| 3rd Inventive Array (4 package array) | | | | | | | | |
| 1st Package in Array | 560-740 | 650 | 18-23 | 20 | 228 | 127 | 1.795 | |
| 2nd Package in Array | 720-1030 | 875 | 23-32 | 27 | 296 | 152 | 1.940 | 2.120 |
| 3rd Package in Array | 1000-1350 | 1175 | 31-42 | 37 | 386 | 178 | 2.172 | |
| 4th Package in Array | 1300-1800 | 1550 | 41-57 | 49 | 490 | 191 | 2.574 | |

Absorbent Article

The absorbent articles of the present disclosure are generally designed and configured to manage bodily exudates such as urine, menses, feces or other vaginal discharges.

In one embodiment, an absorbent article may comprise a chassis comprising a topsheet, a backsheet, and an absorbent core disposed at least partially between the topsheet and the backsheet. The absorbent chassis may comprise a waistband, leg cuffs and or elastic strands. In various embodiments, referring to FIG. 12, an example absorbent article 10 is shown in its flat uncontracted state prior to joining the fastening components 53a and b.

Figure 12:
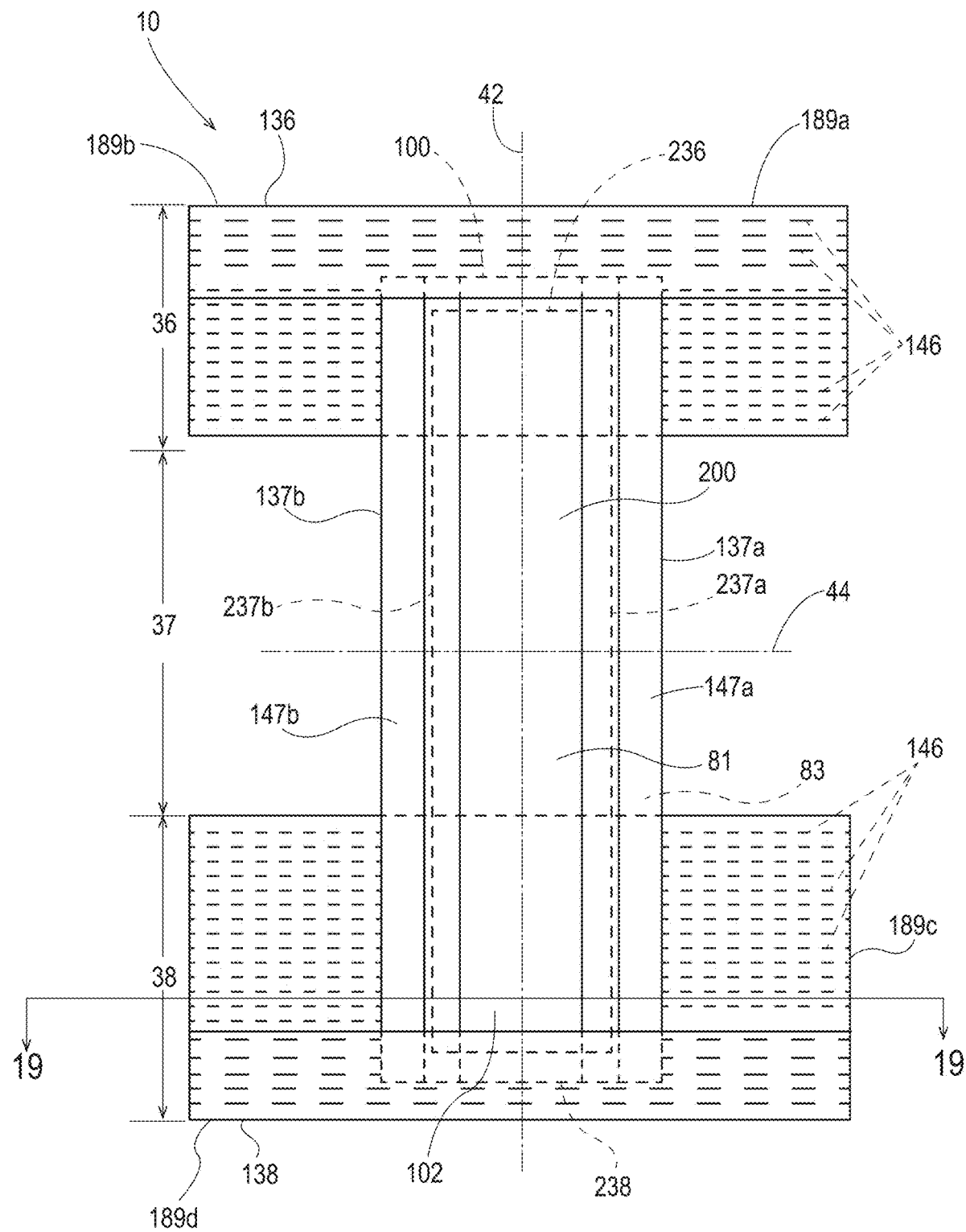
FIG. 12 is a plan view of a pant diaper with a continuous belt in the front and back waist regions.

In one embodiment, referring to FIG. 12, one end portion of the absorbent article 10 may be configured as a front waist region 36 and the longitudinally opposing end portion may be configured as a back waist region 38. An intermediate portion of the absorbent article 10 extending longitudinally between the front waist region 36 and the back waist region 38 may be configured as a crotch region 37. In one embodiment, although not illustrated as such, the length of each of the front waist region 36, the back waist region 38 and the crotch region 37 may be about ⅓ of the length of the absorbent article 10, for example. In other embodiments, the length of each of the front waist region 36, the back waist region 38, and the crotch region 37 may have other dimensions. In various embodiments, the absorbent article 10 may have a laterally extending front waist end edge 136 in the front waist region 36 and a longitudinally opposing and laterally extending back waist end edge 138 in the back waist region 38.

In one embodiment, referring to FIG. 12, a chassis 100 of the absorbent article 10 may comprise a first longitudinally extending side edge 137a and a laterally opposing and second longitudinally extending side edge 137b. Both of the side edges 137 may extend longitudinally between the front waist end edge 136 and the back waist end edge 138. The chassis 100 may form a portion of the laterally extending front waist end edge 136 in the front waist region 36 and a portion of the longitudinally opposing and laterally extending back waist end edge 138 in the back waist region 38. Furthermore, the chassis 100 may comprise an interior surface 102, an exterior surface 104, a longitudinal axis 42, and a lateral axis 44. The longitudinal axis 42 may extend through a midpoint of the front waist end edge 136 and through a midpoint of the back waist end edge 138, while the lateral axis 44 may extend through a midpoint of the first side edge 137a and through a midpoint of the second side edge 137b.

In various embodiments, a portion of or the whole absorbent article 10 may be made to be laterally extensible. The extensibility of the absorbent article 10 may be desirable in order to allow the absorbent article 10 to conform to a body of a wearer during movement by the wearer. The extensibility may also be desirable, for example, in order to allow the caregiver to extend the front waist region 36, the back waist region 38, the crotch region 37, and/or the chassis 100 to provide additional body coverage for wearers of differing size, i.e., to tailor the absorbent article 10 to the individual wearer. Such extension may provide the absorbent article 10 with a generally hourglass shape, so long as the crotch region 37 is extended to a relatively lesser degree than the waist regions 36 and/or 38. This extension may also impart a tailored appearance to the absorbent article 10 during use.

Any or all portions of the absorbent article may comprise a bacteriophage composition as described in U.S. Ser. No. 61/931,229, titled DISPOSABLE ABSORBENT ARTICLES COMPRISING BACTERIOPHAGES AND RELATED METHODS, and filed on Jan. 24, 2014.

Topsheet

Figure 19:
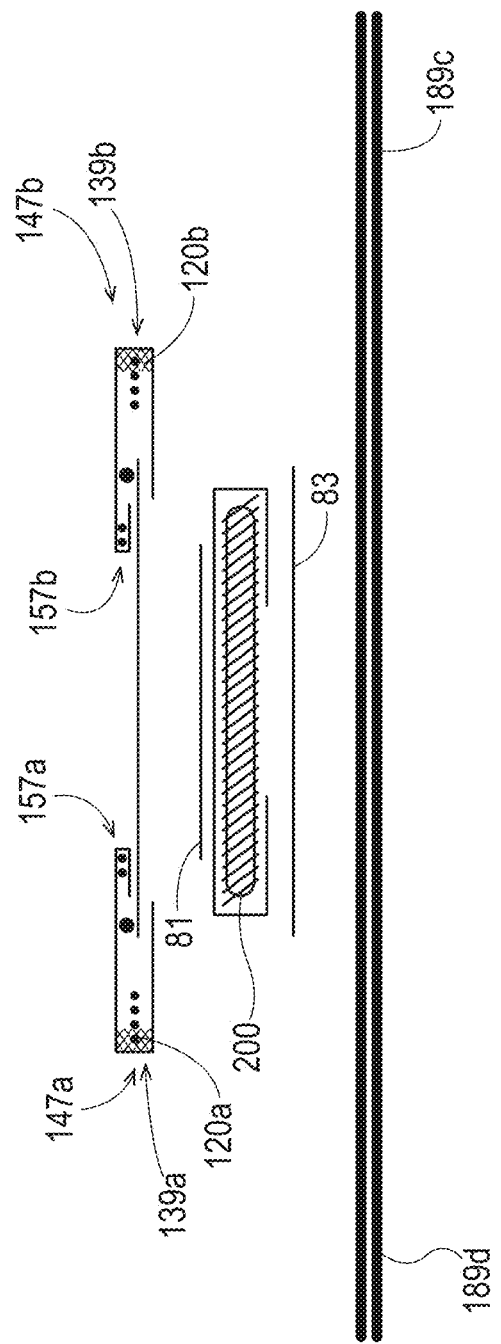
FIG. 19 is a schematic cross section view of a back belt-like flap suitable in one embodiment of the invention, taken along line 19-19 of FIG. 12.

In one embodiment, referring to FIGS. 12 and 19, the absorbent article 10 may comprise a topsheet 81. The topsheet 81 may be compliant, soft feeling, and non-irritating to the wearer's skin and may be elastically stretchable in one or more directions. Further, the topsheet 81 may be liquid pervious, permitting liquids (e.g., menses, urine, and/or runny feces) to penetrate through its thickness. Various topsheets may also comprise a hydrophilic material, for example, which is configured to draw bodily fluids into an absorbent core of the chassis 100 when these fluids are expelled from the body. A suitable topsheet 81 may be manufactured from a wide range of materials, such as woven and nonwoven materials, apertured or hydroformed thermoplastic films, apertured nonwovens, porous foams, reticulated foams, reticulated thermoplastic films, and/or thermoplastic scrims, for example. Suitable apertured films may comprise those described in U.S. Pat. Nos. 3,929,135, 4,324, 246, 4,342,314, 4,463,045, 5,006,394, 5,628,097, 5,916,661, 6,545,197, and 6,107,539.

Apertured film or nonwoven topsheets typically may be pervious to bodily exudates, yet non-absorbent, and have a reduced tendency to allow fluids to pass back through and rewet the wearer's skin. Suitable woven and nonwoven materials may comprise natural fibers, such as, for example, wood or cotton fibers, synthetic fibers, such as, for example, polyester, polypropylene, or polyethylene fibers, or combinations thereof. If the topsheet 81 comprises fibers, the fibers may be spunbond, carded, wet-laid, meltblown, hydroentangled, or otherwise processed, for example, as is generally known in the art.

The topsheet may comprise a skin care lotion. Examples of suitable lotions include, but are not limited to, those described in U.S. Pat. Nos. 5,607,760; 5,609,587; 5,635, 191; 5,643,588; and 5,968,025, and as described in U.S. Application No. 61/391,353.

In one embodiment, the topsheet may comprise graphics (e.g., 116 in FIG. 15) such that depth perception is created as described in U.S. Pat. No. 7,163,528.

Backsheet

Figure 18:
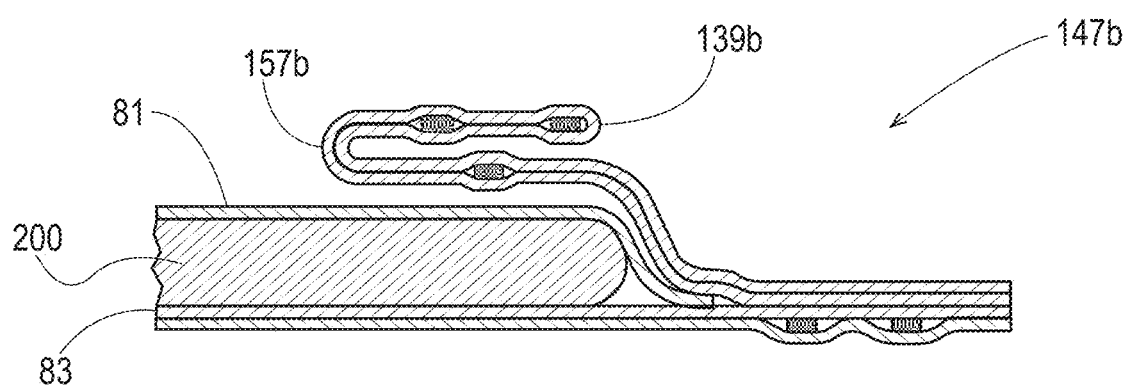
FIG. 18 is a schematic cross section view taken along line 18-18 in FIG. 13 of an example of a folded outer leg cuff suitable in one embodiment of the invention.

In one embodiment, referring to FIGS. 18 and 19, for example, the absorbent article 10 may comprise a backsheet 83. The backsheet 83 may be impervious, or at least partially impervious, to fluids or body exudates (e.g., menses, urine, and/or runny feces) and may be manufactured from a thin plastic film, although other flexible liquid impervious materials may also be used. The backsheet 83 may prevent the body exudates or fluids absorbed and contained in an absorbent core of the absorbent article 10 from wetting articles which contact the absorbent article 10, such as bedsheets, pajamas, clothes, and/or undergarments. The backsheet 83 may comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). A suitable backsheet may comprise a polyethylene film having a thickness of from about 0.012 mm (0.5 mils) to about 0.051 mm (2.0 mils). Examples of polyethylene films are manufactured by Clopay Corporation of Cincinnati, Ohio, under the designation BR-120 and BR-121, and by Tredegar Film Products of Terre Haute, Ind., under the designation XP-39385.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m$^2$ to about 35 g/m$^2$. The backsheet can be typically positioned adjacent the outer-facing surface of the absorbent core and can be joined thereto. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986. Another suitable attachment device including several lines of adhesive filaments swirled into a spiral pattern is illustrated by the apparatus and methods shown in U.S. Pat. Nos. 3,911,173; 4,785,996; and 4,842,666. Alternatively, the attachment device may include heat bonds, pressure bonds, ultrasonic bonds, dynamic mechanical bonds, or any other suitable attachment device or combinations of these attachment devices.

In one embodiment, the backsheet 83 may be embossed and/or matte-finished to provide a more cloth-like appearance. Further, the backsheet 83 may permit vapors to escape from the absorbent core of the absorbent article 10 (i.e., the backsheet 83 is breathable) while still preventing, or at least inhibiting, fluids or body exudates from passing through the backsheet 83. In one embodiment, the size of the backsheet 83 may be dictated by the size of the absorbent article 10 and the design or configuration of the absorbent article 10 to be formed, for example.

Absorbent Core

In various embodiments, referring to FIGS. 18 and 19, the absorbent article 10 may comprise an absorbent core (also referred to as an "absorbent member" or "absorbent assembly" or "absorbent structure" or "absorbent composite") 200 that is disposed between the topsheet 81 and the backsheet 83. The absorbent core 200 may comprise a laterally extending front edge 236 in the front waist region 36, a longitudinally opposing and laterally extending back edge 238 in the back waist region 38, a first longitudinally extending side edge 237a, and a laterally opposing and second longitudinally extending side edge 237b. Both of the side edges 237 may extend longitudinally between the front edge 236 and the back edge 238. In one embodiment, more than one absorbent core 200 or more than one absorbent core layer may be provided in an absorbent article 10, for example. The absorbent core 200 may be any suitable size or shape that is compatible with the absorbent article 10. Example absorbent structures for use as the absorbent core 200 of the present disclosure that have achieved acceptance and commercial success are described in U.S. Pat. Nos. 4,610,678; 4,673,402; 4,888,231; and 4,834,735.

In one embodiment, suitable absorbent cores may comprise cellulosic airfelt material. For instance, such absorbent cores may comprise less than about 40%, 30%, 20%, 10%, 5%, or even 1% of the cellulosic airfelt material as determined by weight. Additionally, such an absorbent core may be primarily comprised of an absorbent gelling material in amounts of at least about 60%, 70%, 80%, 85%, 90%, 95%, or even about 100% as determined by weight. Furthermore, a portion of the absorbent core may comprise a microfiber glue (if applicable). Such absorbent cores, microfiber glues, and absorbent gelling materials are described in U.S. Pat. Nos. 5,599,335; 5,562,646; 5,669,894; 6,790,798; and 7,521,587 and in U.S. Pat. Publ. No. 2004/0158212.

In one embodiment, the core, including multiple layers making up the core system, may be printed and embossed as described in U.S. Pat. No. 8,536,401.

In one embodiment, the core may be separable from the chassis as disclosed in U.S. Pat. Nos. 6,989,006; 7,381,202; 7,175,613; 7,824,386; 7,766,887; and 6,989,005. In such embodiments, the measurements described in this disclosure may be made to the chassis alone or may be made to the chassis in combination with the separable core/absorbent assembly.

In one embodiment, the absorbent article of the present disclosure, and particularly, a portion where the absorbent member is disposed, may have a body fluid absorption rate greater than 3 g/sec according to U.S. Pat. No. 6,649,810. According to U.S. Pat. No. 6,649,810, the expression "the portion (of the absorbent article) where the absorbent member is disposed" is intended to mean the portion occupied by the absorbent member when the absorbent article is flatly unfolded and seen in its plan view.

In one embodiment, the absorbent structure may have an intake factor greater than 3 according to U.S. Pat. No. 7,073,373, wherein the intake factor is defined as the absorbent core permeability divided by the normalized retention capacity (which is defined by the Retention Capacity Test—also according to U.S. Pat. No. 7,073,373).

In one embodiment, the absorbent composite has a body fluid absorption greater than 75 g/100 cm$^2$, according to U.S. Pat. No. 6,649,810.

In one embodiment, a target location of the absorbent article may have a wicking value greater than 36%, according to U.S. Pat. No. 6,383,960.

In one embodiment, the absorbent article may have a bending stiffness between 0.05-1.0 gf, according to U.S. Pat. No. 5,810,796.

In one embodiment, the absorbent article may have a crotch fluid absorption rate greater than 3 g/sec according to U.S. Pat. No. 6,649,810. In one embodiment, a freeze-dried composite of the absorbent composite may have an intake rate of at least about 1.9 cubic centimeters (cc) of liquid/second at 80% composite saturation according to U.S. Pat. No. 6,689,934.

Leg Cuffs

Figure 13:
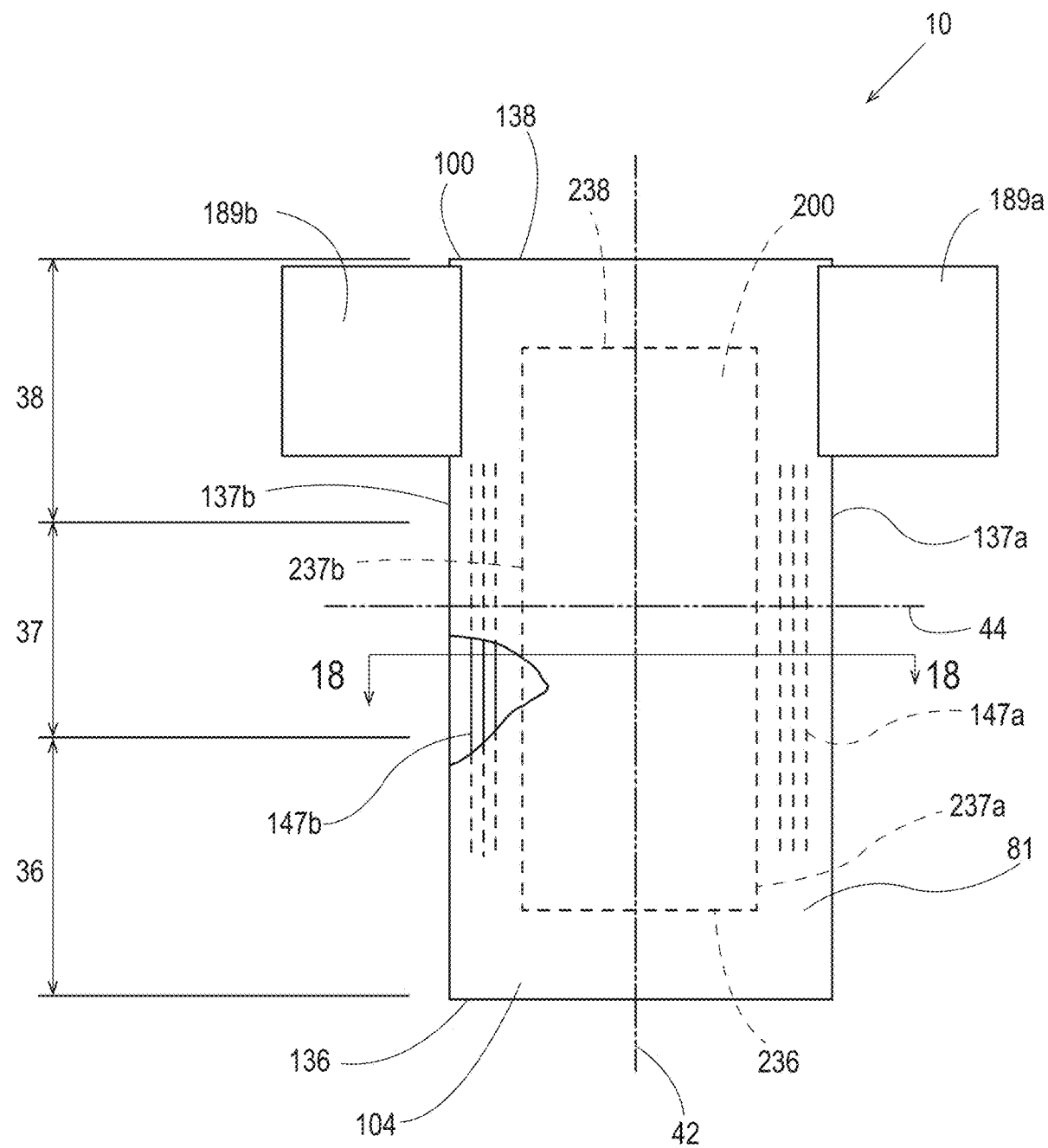
FIG. 13 is a partially cut away plan view of a pant diaper with a pair of flaps, wherein the wearer-facing interior of the diaper faces the viewer.
Figure 14:
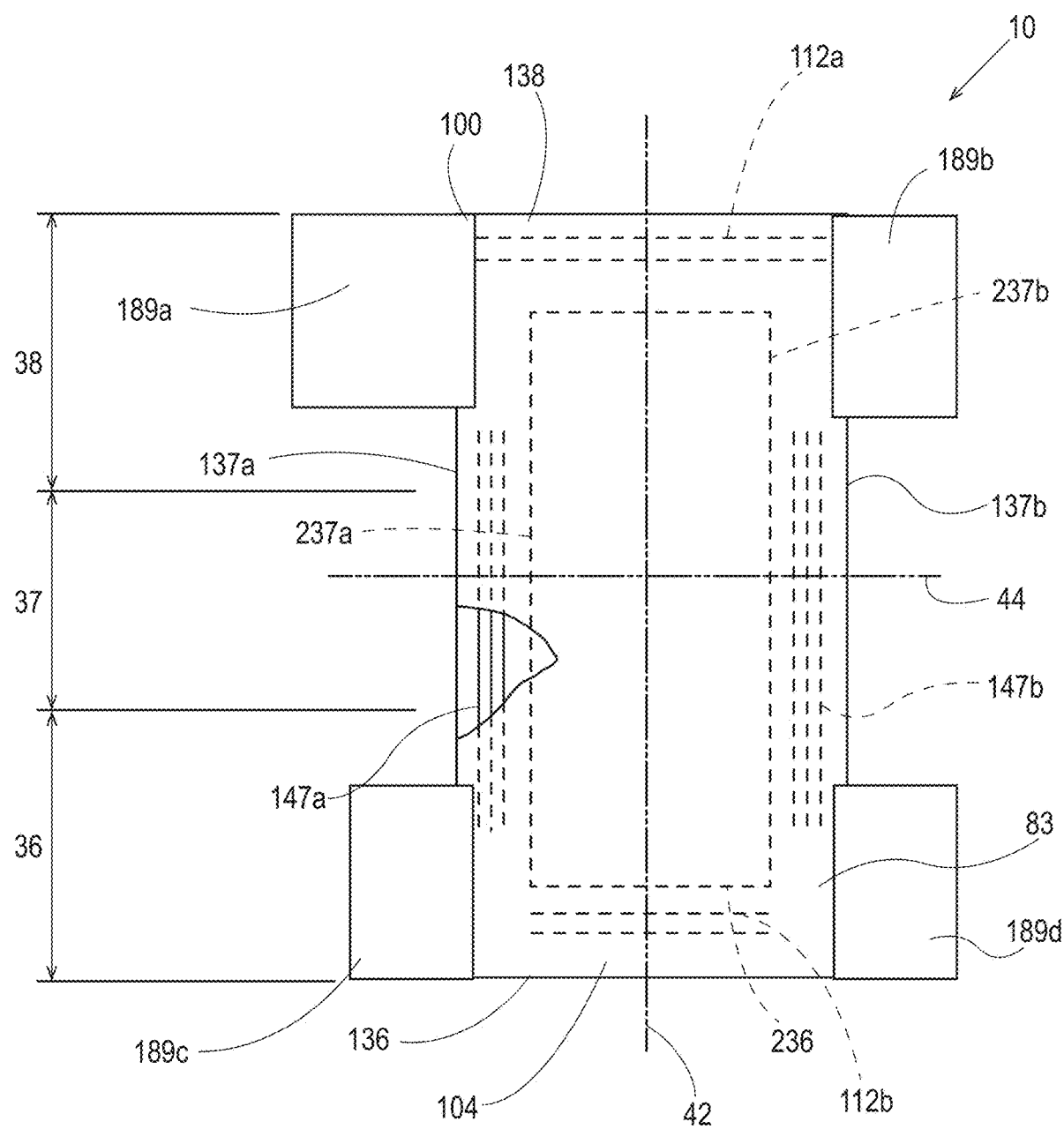
FIG. 14 is a partially cut away plan view a pant diaper with front and rear flaps, wherein the garment-facing exterior of the diaper faces the viewer.

In one embodiment, referring to FIGS. 13 and 14, the chassis 100 of the absorbent article 10 may comprise longitudinally extending and laterally opposing leg cuffs 147a and 147b that are disposed on the interior surface of the chassis 100 that faces inwardly toward the wearer and contacts the wearer. The leg cuffs 147a and 147b may comprise one or more elastic gathering members disposed at or adjacent the proximal edge of one or both of the leg cuffs 147. In addition, the elastic gathering members of the leg cuff may also comprise one or more elastic strands 146 disposed at or adjacent the distal edge of one or both of the leg cuffs 147. The elasticized leg cuffs 147 may comprise several embodiments for reducing the leakage of body exudates or fluids in the leg regions. The elasticized leg cuffs 147 are sometimes referred to as leg bands, barrier cuffs, elastic cuffs, or gasketing cuffs. Suitable elasticized leg cuffs 147 may comprise those described in U.S. Pat. Nos. 3,860,003, 4,909,803, 4,695,278, 4,795,454, 4,704,115, and 4,909,803, and U.S. Pat. Publ. No. 2009/0312730. The leg cuffs 147 may be formed by folding portions of the chassis 100 laterally inward, i.e., toward the longitudinal axis 42, to form both the respective leg cuffs 147 and the side edges 137a and b of the chassis 100. In other embodiments, the leg cuffs 147 may be formed by attaching an additional layer or layers to the chassis 100 at or adjacent to each of the respective side edges 137a and 137b of the chassis 100. In one embodiment, the chassis 100 may also comprise other elastics disposed adjacent the side edges 137 which may cause the article 10 to form into a "U" shape when allowed to relax thereby pulling the interior surface 102 of the front waist region 36 toward the interior surface 102 of the back waist region 38.

In one embodiment, each leg cuff 147 may comprise a proximal edge 157a and 157b. These edges 157a and 157b are positioned proximate to the longitudinal axis 42 compared to distal edges 139a and 139b. The leg cuffs 147 may overlap the absorbent core 200, i.e., the proximal edges 157a and 157b lie laterally inward of the respective side edges 237a and 237b of the absorbent core 200. Such an overlapped configuration may be desirable in order to impart a more finished appearance to the absorbent article 10 than that imparted by a non-overlapped configuration. In other embodiments, the leg cuffs 147 may not overlap the absorbent core 200.

In one embodiment, each leg cuff 147 may be attached to the interior surface 102 of the chassis 100 in a leg cuff attachment zone (not shown) adjacent to the front waist end edge 136 and in a longitudinally opposing leg cuff attachment zone (not shown) adjacent to the back waist end edge 138. In one embodiment, between the leg cuff attachment zones, the proximal edge 157 of the leg cuff 147 remains free, i.e., not attached to the interior surface 102 of the chassis 100 or to the absorbent core 200. Also, between the longitudinally opposing leg cuff attachment zones, each leg cuff 147 may comprise one or more (specifically including one, two, three, or four elastic strands per leg cuff 147) longitudinally extensible cuff elastic gathering members 159 that may be disposed at or adjacent to the proximal edge 157 of the leg cuff 147 by any suitable methods. Each of such cuff elastic gathering members 159 may be attached over the leg cuff's entire length or over only a portion of the leg cuff's length. For example, such cuff elastic gathering members 159 may be attached only at or near the leg cuff's longitudinally opposing ends and may be unattached at the middle of the leg cuff's length. Such cuff elastic gathering members 159 may be disposed in the crotch region 37 and may extend into one or both of the front waist region 36 and the back waist region 38. For example, an elastic gathering member 159 may be attached at or adjacent to the proximal edge 157 of each of the leg cuffs 147 and extends into both the front waist region 36 and the back waist region 38.

In various embodiments, each cuff elastic gathering member 159 may be enclosed inside a folded hem for example. In various embodiments, the cuff elastic gathering members 159 may be sandwiched between two layers forming the leg cuff 147, by two layers of the chassis 100, or may be attached on a surface of the chassis 100 or the leg cuff 147 and remain exposed.

In one embodiment, when stretched, the cuff elastic gathering member 159 disposed adjacent to each leg cuff's proximal edge 157 allows the leg cuff proximal edge 157 to extend to the flat uncontracted length of the chassis 100, e.g., the length of the chassis 100. When allowed to relax, the cuff elastic gathering member 159 contracts to pull the front waist region 36 and the back waist region 38 toward each other and, thereby, bend the article 10 into a "U" shape in which the interior of the "U" shape may be formed by the portions of the article 10 that are intended to be placed toward the body of the wearer (i.e., interior surface 102). Because each of the proximal edges 157 remains free between the longitudinally oriented leg cuff attachment zones, the contractive force of the elastic gathering member 159 may lift the proximal edge 157 of the leg cuff 147 away from the interior surface 102 of the chassis 100. This lifting of the proximal edges 157 when the article 10 is in the relaxed condition lifts the leg cuffs 147 into a position to serve as side barriers to prevent, or at least inhibit, leakage of bodily exudates.

Waistband

In one embodiment, referring to FIG. 14, the article 10 may comprise an elasticized waistband 112a and b. The elasticized waistband may provide improved fit and containment and may be configured to elastically expand and contract laterally to dynamically fit a wearer's waist. The elasticized waistband may extend longitudinally outwardly from the waist edge of the absorbent article 10 toward the waist edge of the absorbent core 200. In one embodiment, the absorbent article 10 may have two elasticized waistbands, one positioned in the back waist region 38 and one positioned in the front waist region 36, although other pant embodiments may be constructed with a single elasticized waistband. The elasticized waistband may be constructed in a number of different configurations including those described in U.S. Pat. Nos. 4,515,595 and 5,151,092.

In one embodiment, the elasticized waistbands may comprise materials that have been "prestrained" or "mechanically prestrained" (i.e., subjected to some degree of localized pattern mechanical stretching to permanently elongate the material). The materials may be prestrained using suitable deep embossing techniques. In other embodiments, the materials may be prestrained by directing the material through an incremental mechanical stretching system as described in U.S. Pat. No. 5,330,458. The materials may then be allowed to return to their substantially untensioned condition, thus forming a zero strain stretch material that is extensible, at least up to the point of initial stretching. Examples of zero strain materials are disclosed in U.S. Pat. Nos. 2,075,189, 3,025,199, 4,107,364, 4,209,563, 4,834,741, and 5,151,092.

Flaps

The flaps 189 (a-d) may be discrete from or integral with the chassis 100. A discrete flap is formed as separate element, which is joined to the chassis 100. In some embodiments, this includes a plurality of flaps, e.g. 2 or 4 (often referred to as ear panels or side flaps) being joined to the side edges 137 a and b of the chassis in the front and/or rear waist regions 36 and 38 (see FIGS. 12-17). In other embodiments this may include a front and/or back belt-like flaps ("belts") being joined across the front and back (or rear) waist regions of the chassis 100, at least across end edges of the chassis 136 and 138 (see FIGS. 12 and 19). In some embodiments the waistbands 112 can overlap the flaps to create a continuous belt-like structure (see FIG. 14).

The belt-like flaps and may comprise an inner nonwoven layer and an outer nonwoven layer and elastics there between. The inner and outer nonwoven layers may be joined using adhesive or thermoplastic bonds. Various suitable belt-like flap configurations can be found in U.S. Pub. No. 2013-0211363.

An integral flap is a portion, one or more layers, of the chassis that projects laterally outward from the longitudinal edge. The integral flap may be formed by cutting the chassis to include the shape of the flap projection.

While many of the embodiments illustrated in this application having belt-like flaps are pant articles, taped articles may have belt-like flaps disposed in one or both waist regions as well.

The structure of flaps play an important role in the functionality of the absorbent article and are fundamentally different than the elastics used in underwear. As mentioned above, incontinence events, such as SUI and UUI, can result in a high flow rate and/or a full bladder release. The amounts of urine expelled during the incontinence events can vary wildly given the type of urinary incontinence as well as other circumstances such as time since last bathroom visit, amount of fluid intake, day or night, etc. Loadings can range from as low as a few drops of urine to loadings as high as 600 mls. It is not unusual to have single loadings as high as 300, 400 and even 500 mls. These levels of loading present a significant downward force associated with the loading which can be a pound or more. This downward force must be compensated for by the absorbent article chassis in order to minimize sagging, gapping and leakage. In order to sustain the fit of the article even after loading the article comprises elastomeric element(s) 146, including films and/or strands) that are disposed proximate to and along the side seams 280a and b (see, for example, FIG. 15, where the elastomeric elements 146 terminate proximate to and along the length of the seams 280a and b) of the article and extend laterally from one side toward the other. These elastomeric element(s) should create a normal force against the body sufficient to anchor the article. The location of the elastomeric element(s), as well as the forces exerted by the elastomeric element(s) can be varied to ensure proper anchoring at the hips and along the body specifically across the front waist region and in the back waist region. One form of anchoring beneficial for sustaining the fit of a loaded article is disclosed in U.S. Pat. No. 5,358,500 Absorbent Articles Providing Sustained Dynamic Fit issued Oct. 25, 1994 to LaVon, et al. It should also be noted that regular underwear with elastic along the waist edge and leg edges would not typically provide sufficient support to sustain the fit of the underwear if a weight of 300-600 grams was applied to the crotch region of the underwear.

Fastening System

The absorbent article may also include a fastening system. When fastened, the fastening system interconnects the front waist region 36 and the rear waist region 38 resulting in a waist circumference that may encircle the wearer during wear of the absorbent article 10. This may be accomplished by flaps 189 *a* and *b* in the back waist region interconnecting with flaps 189 *c* and *d* in the front waist region or by flaps in the back waist region interconnecting with the chassis 100 in the front waist region. The fastening system may comprises a fastener 53 *a* and *b* such as tape tabs, hook and loop fastening components, interlocking fasteners such as tabs & slots, buckles, buttons, snaps, and/or hermaphroditic fastening components, although any other known fastening means are generally acceptable. The fasteners may releasably engage with a landing zone 118, which may be a woven or nonwoven. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system may also provide a means for holding the article in a disposal configuration as disclosed in U.S. Pat. No. 4,963,140. The fastening system may also include primary and secondary fastening systems, as disclosed in U.S. Pat. No. 4,699,622. The fastening system may be constructed to reduce shifting of overlapped portions or to improve fit as disclosed in U.S. Pat. Nos. 5,242,436; 5,499,978; 5,507,736; and 5,591,152.

Identical or Substantially Identical Chassis

As disclosed in U.S. Pub. No. 2013-0211355, it may be desirable to offer an array of packages for fitting different sized wearers, but comprising identical or substantially identical chassis. For instance, an array may comprise a first package comprising a first size of absorbent articles and a second package may comprise a second size of absorbent articles, where the first and second packages comprise identical or substantially identical chassis as described in U.S. Pub. No. 2013-0211355. More particularly, the first package may comprise a first chassis and the second package may comprise a second chassis, where each of the first and second chassis comprise the same dimensions of one or more of: core width at the lateral centerline, core width at one of the front or rear core end, a distance from a left outer cuff distal edge to a right outer cuff distal edge, a distance from a left inner cuff distal edge to a left outer cuff distal edge, a distance from a left inner cuff proximal edge to a right inner cuff proximal edge, a distance from a left inner cuff proximal edge to a left outer cuff distal edge, a free height of the inner cuff, inner cuff hem fold width, inner cuff elastics length, outer cuff elastics length, core length, and backsheet width.

Further, each of the first and second chassis may comprise identical chemical compositions of one or more of a topsheet, backsheet film, backsheet nonwoven, core super absorbent polymers, core pulp, core nonwoven, core tissue, leg cuff film, leg cuff nonwoven, super absorbent polymer adhesive, core nonwoven adhesive, leg cuff elastic adhesive, and backsheet nonwoven/film adhesive.

And, each of the first and second chassis may comprise the same basis weight of one or more of the topsheet, backsheet film, backsheet nonwoven, core super absorbent polymers, core pulp, leg cuff nonwoven, leg cuff film, super absorbent polymer adhesive, leg cuff adhesive, and backsheet nonwoven/film adhesive.

And, each of the first and second chassis may comprise compositionally identical core super absorbent polymers. The first and second chassis may have identical component cross sectional order and disposition in at least one of the front waist region, back waist region, and crotch region. The inner leg cuffs of the first and second chassis may be composed of the compositionally identical materials.

And, the core adhesives of the first and second chassis may be the same adhesive(s). The first and second chassis may comprise core super absorbent polymers that are in the same chemical class and subclass.

And, each of the first and second chassis may comprise first and second wetness indicators, respectively, and wherein the first and second wetness indicators are compositionally identical.

Further, the inner leg cuffs of the first and second chassis may have identical component cross sectional order and disposition in at least one of the front waist region, back waist region, and crotch region. The distance from the left outer cuff distal edge to a right outer cuff distal edge may the same. The distance from the left inner cuff proximal edge to left outer cuff distal edge may be the same. The distance from the left inner cuff proximal edge to the right inner cuff proximal edge is the same. The lengths of the inner and outer cuffs are the same.

In some embodiments, different size offerings in an array may have identical or substantially identical chassis as the flaps or belts may be used to enable the absorbent article to fit different sized wearers. For example, first and second absorbent articles may have identical chassis (compositionally, dimensionally, cross-sectionally), but the first article may have a different length due to disposition of the belts, such that the first article may be targeted to fit a smaller wearer than the second article. As a second example, first and second absorbent articles may have identical chassis (compositionally, dimensionally, cross-sectionally), but the first article may have a different length and/or width due to the size of the belts, such that the first article may be targeted to fit a smaller wearer than the second article.

In some embodiments, first and second absorbent articles may have identical chassis compositionally, but not dimensionally, and not cross-sectionally. In some embodiments, first and second absorbent articles may have identical chassis dimensionally, but not compositionally, and not cross-sectionally. In some embodiments, first and second absorbent articles may have identical chassis cross-sectionally, but not dimensionally, and not compositionally. In still other embodiments, first and second absorbent articles may have two, but not three of (1) compositionally, (2) dimensionally, and (3) cross-sectionally identical chassis.

Test Methods

Product Measurement Preparation

All measurements are conducted at 22° C.+/−2° and 50% RH+/−20%.

Purpose

This method is used to prepare pant type products for subsequent dimensional measurement. The method provides a consistent means of opening a product that has been removed from a bag. This method is applicable to all forms of pant products. A constant rate of extension tensile testing machine with computer interface is used.

A load cell is chosen so that the load cell capacity ensures accuracy of a 5N load to within 0.1N.

Sample Holder Apparatus

Figure 20:
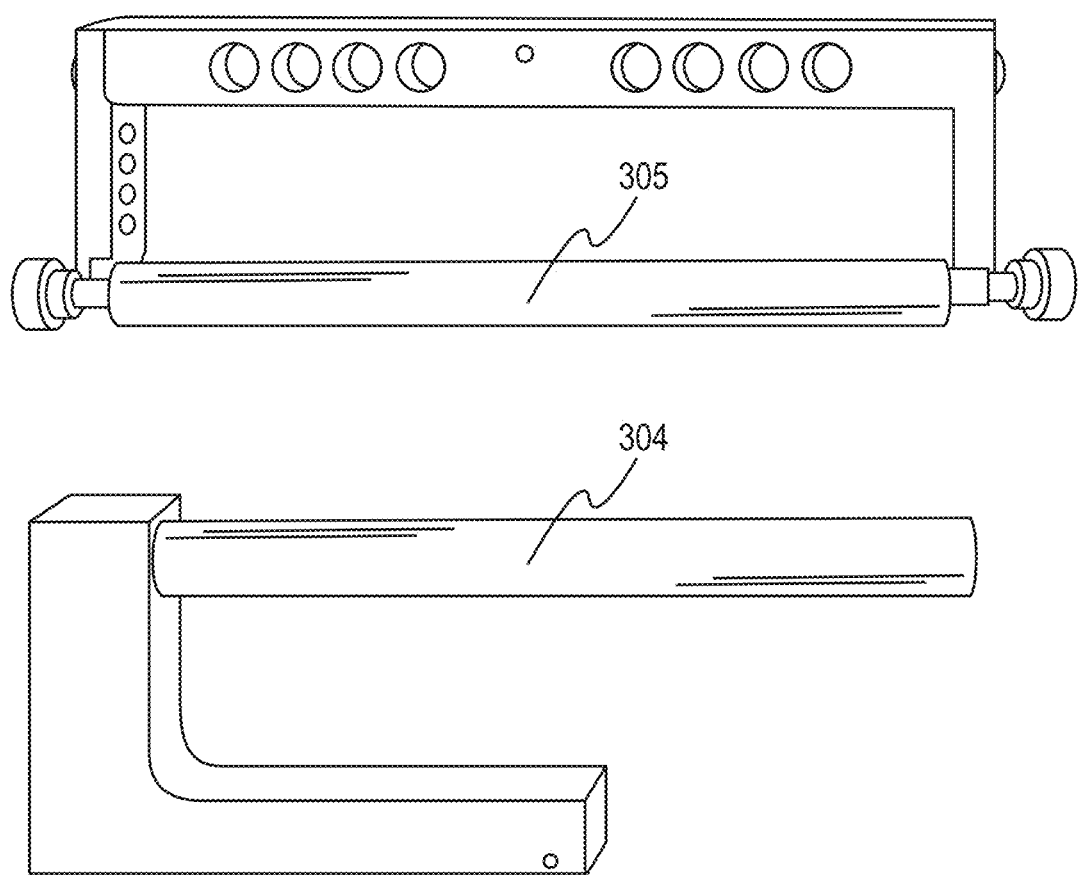
FIG. 20 shows Bar C (304) and Bar O (305) of the Sample Holder Apparatus

"C" (304) and "O" (305) Bar attachments each with a rod radius of 9.50 mm that extend longer than the length of the longest side seam. Refer to FIG. 20. The bars are mounted horizontally in the tensile tester with their longitudinal axes in the same vertical plane and with upper bar mounted directly above the lower bar.

Equipment Set Up

Calibrate tensile tester equipment according to the instrument manufacturer's recommendations.

Figure 21:
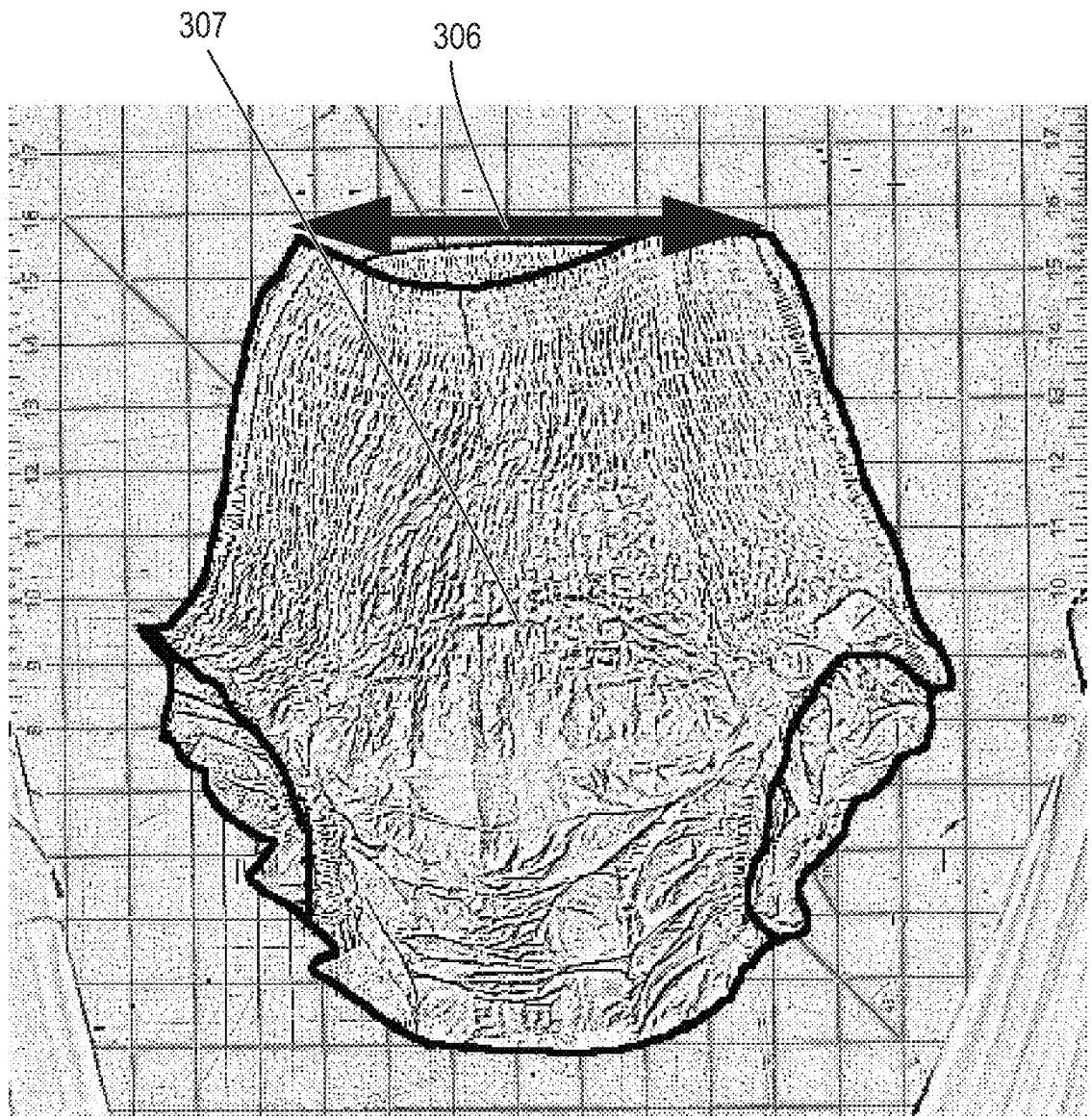
FIG. 21 shows a flat, unfolded pant.

The initial gauge length is determined by removing 10 sample products from the bag, unfolding the pant products (307) and laying them flat as illustrated in FIG. 21, below and measuring the distance between the sides of the pant at the waist as shown (306). The average of the waist measurement will be used as the initial gauge length for the specific set of specimens. The initial gauge length is the distance from the uppermost edge of the upper bar to the lowermost edge of the lower bar.

Figure 22:
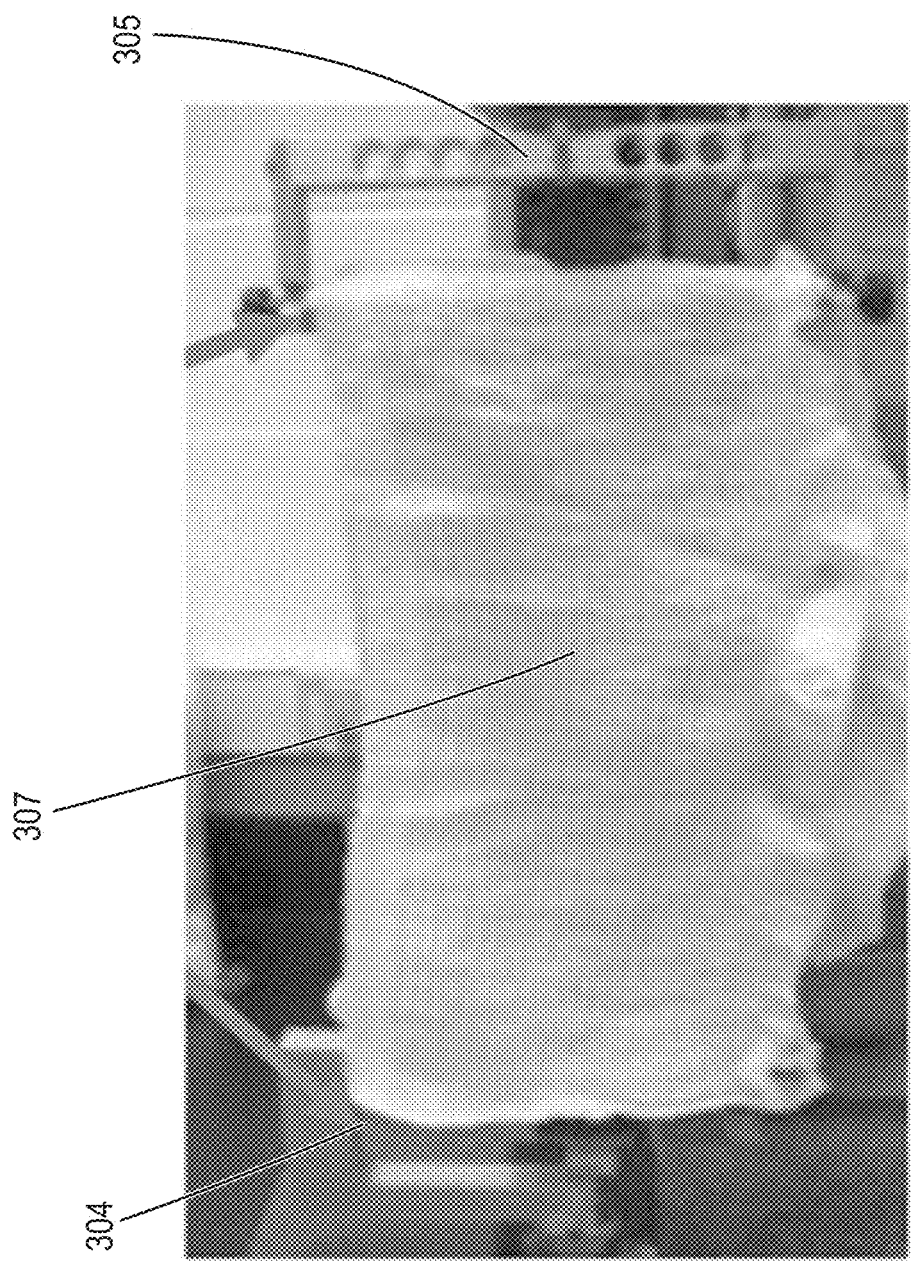
FIG. 22 shows a pant in the testing apparatus.

Apply the whole product (307) to the bars as shown in FIG. 22 while minimizing manipulation of the specimen.

Pull Sample to 5N Force then hold for 10 seconds. Return to initial gauge length.

Crosshead Speed=254.0 mm/min, Data acquisition rate=50 Hz.

Cycles=1

Remove the specimen from the bars while minimizing manipulation. Lay the specimen flat with the front side facing upward as shown in FIG. 6.

Repeat for all 10 specimens

Physical Measurements

Each of the measurements below is to be conducted on 10 separate like specimens and the average of the 10 separate like specimens is considered to be the measurement for that specific specimen set.

Relaxed Product Length (300)

Relaxed Product Length is the longitudinal distance between the longitudinally distal most point in the crotch region and the longitudinally distal most point along the front waist edge. The longitudinal distance is measured parallel to the longitudinal axis of the product. Refer to FIG. 6.

Relaxed Product Hip Width (301)

Relaxed Product Hip Width is the lateral distance from the laterally distal most point of the left side edge of the product at the upper edge of the left leg opening to the laterally distal most point of the right side edge of the product at the upper edge of the right leg opening. Refer to FIG. 6. The lateral distance is measured perpendicular to the longitudinal axis of the product.

Relaxed Product Waist Width (302)

Relaxed Product Waist Width is the lateral distance from the distal most point at the right side of the front waist edge to the distal most point at the left side of the front waist edge. The lateral distance is measured perpendicular to the longitudinal axis of the product. Refer to FIG. 6.

Relaxed Product Side Length (303)

Relaxed Product Side Length is the linear distance from the point of intersection between the waist edge and the side edge of the product to the point of intersection between the top of the leg opening and the same side edge of the product. The relaxed product side length measurement is the average of the measurements from the left and right sides of the product. Refer to FIG. 6.

Each of the measurements above is recorded to within +/−1.0 mm.

What is claimed is:

1. An array of packages comprising two or more different sizes of disposable absorbent articles, the array comprising:
    a first package comprising a first disposable absorbent article, the first absorbent article comprising a first topsheet, a first backsheet, a first absorbent core and a first pair of side seams, the first absorbent article being a first size and in a closed form;
    a second package comprising a second disposable absorbent article, the second absorbent article comprising a second topsheet, a second backsheet, a second absorbent core and a second pair of side seams, the second absorbent article being a second size and in a closed form;
    wherein the second size is larger than the first size;
    wherein the second absorbent article has both of:
        (a) a larger Relaxed Product Side Length than the first absorbent article; and
        (b) a larger Relaxed Product Length than the first absorbent article;
    wherein a Product Length-to-Side Silhouette of the second absorbent article is equal to or greater than a Product Length-to-Side Silhouette of the first absorbent article; and
    wherein the first package and the second package are in the same array.

2. The array of packages of claim 1, wherein the array further comprises a third package comprising a third disposable absorbent article, wherein an Array Average Product Length-to-Side Silhouette of the first, second, and third packages is from about 1.2 to about 1.7.

3. The array of packages of claim 1, wherein the array further comprises a third package comprising a third disposable absorbent article, wherein the third absorbent article has one or more of:
    (a) a larger Relaxed Product Side Length than the first absorbent article; and
    (b) a larger Relaxed Product Length than the first absorbent article;
    wherein the third package has a Product Length-to-Side Silhouette equal to or greater than a Product Length-to-Side Silhouette of at least one of the first and second absorbent articles.

4. The array of packages of claim 1, wherein the first and second absorbent articles of the first and second packages comprise at least substantially identical chassis with regard to chemical composition.

5. The array of packages of claim 2, wherein the first and second absorbent articles of the first and second packages comprise chassis having identical cross-sectional dispositions in at least one of a front, back, or crotch region.

6. The array of packages of claim 1, wherein at least one of the first and second pair of side seams are refastenably engaged.

7. The array of packages of claim 2, wherein the third package has a Product Length-to-Side Silhouette is greater than a Product Length-to-Side Silhouette of each of the first and second absorbent articles.

8. The array of packages of claim 3, wherein the third package has a Product Length-to-Side Silhouette is greater than a Product Length-to-Side Silhouette of the first absorbent article, but less than the and second absorbent article.

9. The array of packages of any of claim 1, wherein an Array Average Product Length-to-Side Silhouette of the first and second packages is from about 1.2 and 1.6.

10. The array of packages of claim 2, wherein an Array Average Product Length-to-Side Silhouette of the first and second packages is from about 1.4 and 1.7.

11. The array of packages of claim 1, wherein the array of packages is an On-Line Array.

12. An adult incontinence disposable absorbent article having a Product Length-to-Side Silhouette from 1.2 to about 1.5, wherein the adult incontinence disposable absorbent article is in closed form.

13. The absorbent article of claim 12 having a Relaxed Product Length is at least 640 mm.

14. The absorbent article of claim 12 having a Relaxed Product Length is at least 500 mm.

15. The absorbent article of claim 12 having a Relaxed Product Length is at least 380 mm.

16. The absorbent article of claim 12 having a Relaxed Product Length is at least 250 mm.

17. An array of packages comprising two or more different sizes of disposable absorbent articles, the array comprising:
- a first package comprising a first disposable absorbent article, the first absorbent article comprising a first topsheet, a first backsheet, a first absorbent core and a first pair of side seams, the first absorbent article being a first size and in a closed form;
- a second package comprising a second disposable absorbent article, the second absorbent article comprising a second topsheet, a second backsheet, a second absorbent core and a second pair of side seams, the second absorbent article being a second size and in a closed form;
- wherein the second size is larger than the first size;
- wherein the second absorbent article has a larger Relaxed Product Side Length than the first absorbent article;
- wherein a Product Length-to-Side Silhouette of the second absorbent article is equal to or greater than a Product Length-to-Side Silhouette of the first absorbent article; and
- wherein the first package and the second package are in the same array.

18. An On-Line Array of packages comprising two or more different sizes of disposable absorbent articles, the On-Line Array comprising:
- an on-line offering of a first package comprising a first disposable absorbent article by a first source, the first absorbent article comprising a first topsheet, a first backsheet, a first absorbent core and a first pair of side seams, the first absorbent article being a first size and in closed form;
- an on-line offering of a second package comprising a second disposable absorbent article by the first source, the second absorbent article comprising a second topsheet, a second backsheet, a second absorbent core and a second pair of side seams, the second absorbent article being a second size and in closed form;
- wherein the second absorbent article has both of:
  (a) a larger Relaxed Product Side Length than the first absorbent article; and
  (b) a larger Relaxed Product Length than the first absorbent article;
- wherein a Product Length-to-Side Silhouette of the second absorbent article is equal to or greater than a Product Length-to-Side Silhouette of the first absorbent article; and
- wherein the first and second packages comprise the same brand name and/or sub-brand name.

* * * * *